(12) United States Patent
Aeschlimann et al.

(10) Patent No.: US 7,196,180 B2
(45) Date of Patent: Mar. 27, 2007

(54) FUNCTIONALIZED DERIVATIVES OF HYALURONIC ACID, FORMATION OF HYDROGELS IN SITU USING SAME, AND METHODS FOR MAKING AND USING SAME

(75) Inventors: Daniel Aeschlimann, Madison, WI (US); Paul Bulpitt, Madison, WI (US)

(73) Assignee: Orthogene LLC, Sausalito, CA (US)

( * ) Notice: Subject to any disclaimer, the term of this patent is extended or adjusted under 35 U.S.C. 154(b) by 0 days.

(21) Appl. No.: 10/680,000

(22) Filed: Oct. 6, 2003

(65) Prior Publication Data

US 2004/0072793 A1    Apr. 15, 2004

Related U.S. Application Data

(62) Division of application No. 09/156,829, filed on Sep. 18, 1998, now Pat. No. 6,630,457.

(51) Int. Cl.
  *A61K 31/728* (2006.01)
  *A61K 31/738* (2006.01)
(52) U.S. Cl. ............... 536/18.7; 536/124; 514/54; 514/62
(58) Field of Classification Search .......... 536/18.7, 536/124; 514/54, 62
  See application file for complete search history.

(56) References Cited

U.S. PATENT DOCUMENTS

| | | | |
|---|---|---|---|
| 4,517,295 A | 5/1985 | Bracke et al. | 435/101 |
| 4,582,865 A | 4/1986 | Balazs et al. | 524/29 |
| 4,703,108 A | 10/1987 | Silver et al. | 530/356 |
| 4,713,448 A | 12/1987 | Balazs et al. | 536/55.1 |
| 4,780,414 A | 10/1988 | Nimrod et al. | 435/101 |
| 4,784,659 A | 11/1988 | Fleckenstein et al. | 623/1 |
| 4,801,539 A | 1/1989 | Akasaka et al. | 435/101 |
| 4,897,349 A | 1/1990 | Swann et al. | 435/101 |
| 4,957,744 A | 9/1990 | della Valle et al. | 424/401 |
| 4,970,298 A | 11/1990 | Silver et al. | 530/356 |
| 5,017,229 A | 5/1991 | Burns et al. | 106/162 |
| 5,166,331 A | 11/1992 | della Valle et al. | 536/55.1 |
| 5,270,300 A | 12/1993 | Hunziker | 514/12 |
| 5,316,926 A | 5/1994 | Brown et al. | 435/101 |
| 5,336,767 A | 8/1994 | della Valle et al. | 536/55.1 |
| 5,356,883 A | 10/1994 | Kuo et al. | 514/54 |
| 5,368,858 A | 11/1994 | Hunziker | 424/423 |
| 5,413,791 A | 5/1995 | Rhee et al. | 424/422 |
| 5,466,462 A | 11/1995 | Rosenthal et al. | 424/426 |
| 5,468,787 A | 11/1995 | Braden et al. | 523/113 |
| 5,502,081 A | 3/1996 | Kuo et al. | 514/777 |
| 5,512,301 A | 4/1996 | Song et al. | 424/484 |
| 5,512,329 A * | 4/1996 | Guire et al. | 427/508 |
| 5,527,893 A | 6/1996 | Burns et al. | 514/53 |
| 5,565,210 A | 10/1996 | Rosenthal et al. | 424/426 |
| 5,567,806 A | 10/1996 | Abdul-Malak et al. | 530/356 |
| 5,616,568 A | 4/1997 | Pouyani et al. | 514/54 |
| 5,652,347 A | 7/1997 | Pouyani et al. | 536/18.5 |
| 5,693,341 A | 12/1997 | Schroeder et al. | 424/488 |
| 5,700,476 A | 12/1997 | Rosenthal et al. | 424/426 |
| 5,769,899 A | 6/1998 | Schwartz et al. | 623/18 |
| 5,817,303 A * | 10/1998 | Stedronsky et al. | 424/78.02 |
| 5,856,299 A * | 1/1999 | Righetto et al. | 514/8 |
| 5,874,417 A * | 2/1999 | Prestwich et al. | 514/54 |
| 6,025,444 A * | 2/2000 | Waki et al. | 525/293 |
| 6,174,999 B1 * | 1/2001 | Miller et al. | 536/21 |

FOREIGN PATENT DOCUMENTS

| | | |
|---|---|---|
| EP | 506976 | * 10/1992 |
| EP | 1082963 A1 | 3/2001 |
| WO | WO 90/06767 | 6/1990 |
| WO | WO 95/24429 | 9/1995 |
| WO | WO 96/15888 | 5/1996 |
| WO | WO 97/18244 | 5/1997 |
| WO | WO 97/45532 | 12/1997 |
| WO | WO 99/55230 | 11/1999 |

OTHER PUBLICATIONS

Hohenadl et al., "Two Adjacent N-terminal Glutamines of BM-40 (Osteonectin, SPARC) Act as Amine Acceptor Sites in TransglutaminaseC-catalyzed Modification," *J. Biol. Chem.*, 270, pp. 23415-23420 (1995).
Kuo et al., "Chemical Modification of Hyaluronic Acid by Carbodiimides," *Bioconjugate Chem.*, 2, pp. 232-241 (1991).
Noble et al., "Induction of inflammatory gene expression by low-molecular-weight hyaluronan fragments in macrophages, in The Chemistry, Biology and Medical Applications of Hyaluronan and Its Derivatives," T.C. Laurent (ed), Portland Press, London, pp. 219-225 (1998).
Pouyani et al., "Functionalized Derivatives of Hyaluronic Acid Oligosaccharides: Drug Carriers and Novel Biomaterials," *Bioconjugate Chem.*, 5, pp. 339-347 (1994).
Adams, M.E., "Viscosupplementation as articular therapy," in The Chemistry, Biology and Medical Applications of Hyaluronan and Its Derivatives, T.C. Laurent (ed.), Portland Press, London, pp. 243-253 (1998).
Amiel et al., "The chondrogenesis of rib perichondrial grafts for repair for full thickness articular cartilage defects in a rabbit model: A one year postoperative assessment." Connect. Tissue Res. 18, pp. 27-39 (1988).
Balazs and Laurent, "Round table discussion: new applications for hyaluronan," in The Chemistry, Biology and Medical Application of Hyaluronan and Its Derivatives, T.C. Laurent (ed.), Portland Press, London, pp. 325-336 (1998).

(Continued)

*Primary Examiner*—Leigh C. Maier
(74) *Attorney, Agent, or Firm*—Fish & Neave IP Group Ropes & Gray LLP

(57) ABSTRACT

Methods for chemical modification of hyaluronic acid, formation of amine or aldehyde functionalized hyaluronic acid, and the cross-linking thereof to form hydrogels are provided. Functionalized hyaluronic acid hydrogels of this invention can be polymerized in situ, are biodegradable, and can serve as a tissue adhesive, a tissue separator, a drug delivery system, a matrix for cell cultures, and a temporary scaffold for tissue regeneration.

13 Claims, 13 Drawing Sheets

OTHER PUBLICATIONS

Band, P.A., "Hyaluronan derivatives: chemistry and clinical applications," in The Chemistry, Biology and Medical Applications of Hyaluronan and Its Derivatives, T.C. Laurent (ed.), Portland Press, London, pp. 33-43 (1998).

Bitter and Muir, "A Modified Uronic Acid Carbazole Reaction," Anal. Biochem., 4, pp. 330-334 (1962).

Brittberg et al., "Treatment of deep cartilage defects in the knee with autologous chondrocyte transplantation," New Engl. J. Med., 331, pp. 889-895 (1994).

Cha, J.S., "Recent developments in the synthesis of aldehydes by reduction of carboxylic acids and their derivatives with metal hydrides. A review.," Org. Prep. Proc. Int., 21, pp. 451-477 (1989).

Cha et al., "Direct Transformation of Carboxylic Acids into Aldehydes through Acyloxy-9-borabicyclo [3.3.1]nonane," Bull. Korean Chem. Soc., 9, pp. 48-52 (1988).

Chu et al., "Articular cartilage repair using allogeneic perichondrocyte-seeded biodegradable porous polylactic acid (PLA): A tissue-engineering study," J. Biomed. Mat. Res, 29, pp. 1147-1154 (1995).

Curvall et al., "Modification of polysaccharides containing uronic acid residues," Carbohydr. Res., 41, pp. 235-239 (1975).

Dahl et al., "Preparation of Biologically Intact Radioiodinated Hyaluronan of High Specific Radioactivity: Coupling of 125I-Tyramine-Cellobiose to Amino Groups after Partial N-Deacetylation," Anal. Biochem., 175, pp. 397-407 (1988).

Danishefsky and Siskovic, "Conversion of carboxyl groups of mucopolysaccharides into amides of amino acid esters," Carbohydr. Res., 16, pp. 199-205 (1971).

Denlinger, J.L., "Hyaluronan and its derivatives as viscoelastics in medicine," in The Chemistry, Biology and Medical Applications of Hyaluronan and Its Derivatives, T.C. Laurent (ed.), Portland Press, London, pp. 235-242 (1998).

Drobnik, J., "Hyaluronan in drug delivery," Adv. Drug Delivery Rev., 7, pp. 295-308 (1991).

Fraser et al., "Catabolism of hyaluronan," in The Chemistry, Biology and Medical Applications of Hyaluronan and Its Derivatives, T.C. Laurent (ed.), Portland Press, London, pp. 85-92 (1998)

Freed et al., "Joint resurfacing using allograft chondrocytes and synthetic biodegradable polymer scaffolds," J. Biomed. Mat. Res., 28, pp. 891-899 (1994).

Gombotz and Pettit, "Biodegradable Polymers for Protein and Peptide Drug Delivery," Bioconjugate Chem., 6, pp. 332-351 (1995).

Grammatikakis et al., "A Novel Glycosaminoglycan-binding Protein Is the Vertebrate Homologue of the Cell Cycle Control Protein, Cdc37, " J. Biol. Chem., 270, pp. 16198-16205 (1995).

Grande et al., "The Repair of Experimentally Produced Defects in Rabbit Articular Cartilage by Autologous Chondrocyte Transplantation," J. Orthop. Res., 7, pp. 208-218 (1989).

Gustafson, S., "Hyaluronan in drug delivery," in The Chemistry, Biology and Medical Applications of Hyaluronan and Its Derivatives, T.C. Laurent (ed.), Portland Press, London, pp. 291-304 (1998).

Harada et al., "Chondrogenesis and Osteogenesis of Bone Marrow-derived Cells by Bone-inductive Factor," Bone, 9, pp. 177-183 (1988).

Hauselmann et al., "Synthesis and Turnover of Proteoglycans by Human and Bovine Adult Articular Chondrocytes Cultured in Alginate Beads," Matrix, 12, pp. 116-129 (1992).

Hauselmann et al., "Adult human chondrocytes cultured in alginate form a matrix similar to native human articular cartilage," Am J. Physiol., 271, pp. C742-C752 (1996).

Homminga et al., "Perichondral grafting for cartilage lesions of the knee," J. Bone Joint Surg., 72-B, pp. 1003-1007 (1990).

Homminga et al., "Repair of articular defects by perichondrial grafts: Experiments in the rabbit," Acta Orthop. Scand., pp. 326-329 (1989).

Hunziker and Rosenberg, "Repair of Partial-Thickness Defects in Articular Cartilage: Cell Recruitment from the Synovial Membrane," J. Bone Joint Surg., 78-A, pp. 721-733 (1996).

Itay et al., "Use of Cultured Embryonal Chick Epiphyseal Chondrocytes as Grafts for Defects in Chick Articular Cartilage," Clin. Orthop., 220, pp. 284-303 (1987).

Kalb and Cowley, "Hope for Damaged Joints," Newsweek, p. 55, Jan. 29, 1996.

King et al., "Beneficial actions of exogenous hyaluronic acid on wound healing," Surgery, 109, pp. 76-84 (1991).

Knudson, C.B., "Hyaluronan Receptor-directed Assembly of Chondrocyte Pericellular Matrix," J. Cell Biol., 120, pp. 825-834 (1993).

Knudson and Knudson, "Hyaluronan-bindind proteins in development, tissue homeostasis, and disease," FASEB J., 7, pp. 1233-1241 (1993).

Kuettner et al., "Synthesis of Cartilage Matrix by Mammalian Chondrocytes in vitro. I. Isolation, Culture Characteristics, and Morphology," J. Cell Biol., 93, pp. 743-750 (1982).

Kurzer and Douraghi-Zadeh, "Advances in the Chemistry of Carbodiimides," Chem. Rev., 67, pp. 107-152 (1967).

Kvam et al., "Purification and Characterization of Hyaluronan from Synovial Fluid," Anal. Biochem., 211, pp. 44-49 (1993).

Larsen, N.E., "Management of adhesion formation and soft tissue augmentation with viscoelastics: hyaluronan derivatives," in The Chemistry, Biology and Medical Applications of Hyaluronan and Its Derivatives, T.C. Laurent (ed.), Portland Press, London, pp. 267-281 (1998).

Larsen and Balazs, "Drug delivery systems using hyaluronan and its derivatives," Adv. Drug Delivery Rev., 7, pp. 279-293 (1991).

Laurencin et al., "Poly(anhydride) administration in high doses in vivo: Studies of biocompatibility and toxicology," J. Biomed. Mat. Res., 24, pp. 1463-1481 (1990).

Laurent and Fraser, "Hyaluronan," FASEB J., 6, pp. 2397-2404 (1992).

Maleski and Knudson, "Hyaluronan-Mediated Aggregation of Limb Bud Mesenchyme and Mesenchymal Condensation during Chondrogenesis," Exp. Cell Res., 225, pp. 55-66 (1996).

McPherson et al., "Collagen Fibrillogenesis In Vitro: A Characterization of Fibril Quality as a Function of Assembly Conditions," Collagen Rel. Res., 5, pp. 119-135 (1985).

Morgelin et al., "The cartilage proteoglycan aggregate: assembly through combined protein-carbohydrate and protein-protein interactions," Biophys. Chem., 50, pp. 113-128 (1994).

Nakahara et al., "Culture-Expanded Periosteal-Derived Cells Exhibit Osteochondrogenic Potential in Porous Calcium Phosphate Ceramics In Vivo," Clin. Orthop., 276, pp. 291-298 (1992).

O'Driscoll et al., "Durability of Regenerated Articular Cartilage Produced by Free Autogenous Periosteal Grafts in Major Full-Thickness Defects in Joint Surfaces under the Influence of Continuous Passive Motion," J. Bone Joint Surg., 70-A, pp. 595-606 (1988).

Ogamo et al., "Preparation and properties of fluorescent glycosamino-glycuronans labeled with 5-aminofluorescein," Carbohydr. Res., 105, pp. 69-85 (1982).

Parameswaran et al., "Labeling of ε-lysine cross-linking sites in proteins with peptide substrates of factor XIIIa and transglutaminase," Proc. Natl. Acad. Sci. U.S.A., 87, pp. 8472-8475 (1990).

Prestwich et al., "Chemical modification of hyaluronic acid for drug delivery, biomaterials and biochemical probes," in The Chemistry, Biology and Medical Applications of Hyaluronan and Its Derivatives, T.C. Laurent (ed.), Portland Press, London, pp. 43-65 (1998).

Richards and Knowles, "Glutaraldehyde as a Protein Cross-linking Reagent," J. Mol. Biol., 37, pp. 231-233 (1968).

Robinson et al., "Regenerating Hyaline Cartilage in Articular Defects of Old Chickens Using Implants of Embryonal Chick Chondrocytes Embedded in a New Natural Delivery Substance," Calcif. Tissue Int., 46, pp. 246-253 (1990).

Sampath et al., "Recombinant Human Osteogenic Protein-1 (hOP-1) Induces New Bone Formation in Vivo with a Specific Activity Comparable with Natural Bovine Osteogenic Protein and Stimulates Osteoblast Proliferation and Differentiation in Vitro," J. Biol. Chem., 267, pp. 20352-20362 (1992).

Scott, J.E., "Chemical morphology of hyaluronan," in The Chemistry, Biology and Medical Applications of Hyaluronan and Its Derivatives, T.C. Laurent (ed.), Portland Press, London, pp. 7-15 (1998).

Sheng et al., "A Specific Quantitative Colorimetric Assay for L-Asparagine," *Anal. Biochem.*, 211, 242-249 (1993).

Shortkroff et al., "Healing of chondral and osteochondral defects in a canine model: the role of cultured chondrocytes in regeneration of articular cartilage," *Biomaterials*, 17, pp. 147-154 (1996).

Stachan et al., "Hyaluronate in rheumatology and orthopaedics: Is there a role?" *Ann. Rheum. Dis.*, 49, 949-952 (1990).

Vercruysse et al., "Synthesis and in vitro Degradation of New Polyvalent Hydrazide Cross-Linked Hydrogels of Hyaluronic Acid," *Bioconjugate Chem.*, 8, pp. 686-694 (1997).

Vilaseca et al., "Protein Conjugates of Defined Structure: Synthesis and Use of a New Carrier Molecule," *Bioconjugate Chem.*, 4, pp. 515-520 (1993).

Wakitani et al., "Mesenchymal Cell-Based Repair of Large, Full-Thickness Defects of Articular Cartilage," *J. Bone Joint Surg.*, 76-A, pp. 579-592 (1994).

Wakitani et al., "Repair of rabbit articular surfaces with allograft chondrocytes embedded in collagen gel," *J. Bone Joint Surg.*, 71-B, pp. 74-80 (1989).

Wang et al., "Recombinant human bone morphogenetic protein induces bone formation," *Proc. Natl. Acad. Sci. U.S.A.*, 87, pp. 2220-2224 (1990).

Weiss, C., "Viscoseparation and viscoprotection as therapeutic modalities in the musculoskeletal system," in The Chemistry, Biology and Medical Applications of Hyaluronan and Its Derivatives, T.C. Laurent (ed.), Portland Press, London, pp. 255-265 (1998).

Wong, S.S., "Chemistry of protein conjugation and crosslinking," CRC Press, Inc., Boca Raton, FL, p. 27 (1993).

Yang and Moses, "Transforming Growth Factor $\beta$1-induced Changes in Cell Migration, Proliferation, and Angiogenesis in the Chicken Chorioallantoic Membrane," *J. Cell Biol.*, 111, pp. 731-741 (1990).

* cited by examiner

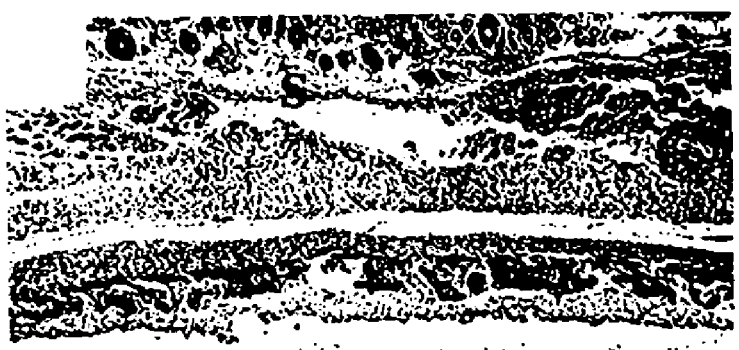
FIG. 7A
FIG. 7B
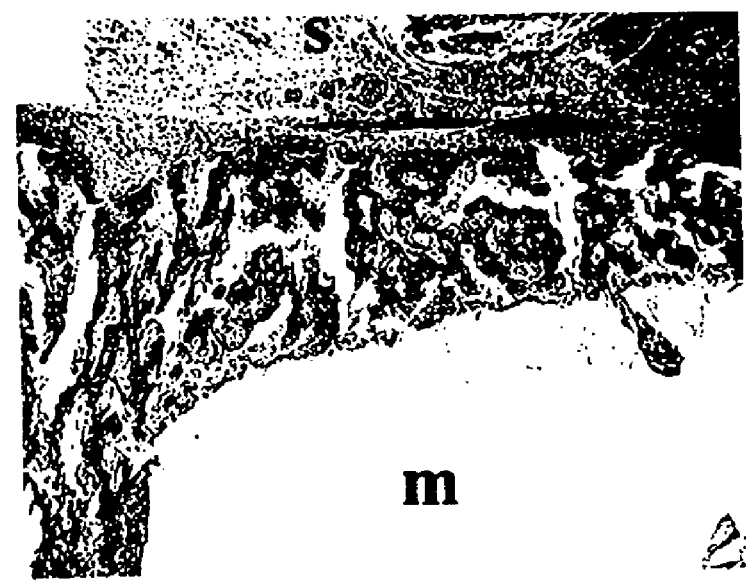
FIG. 7C
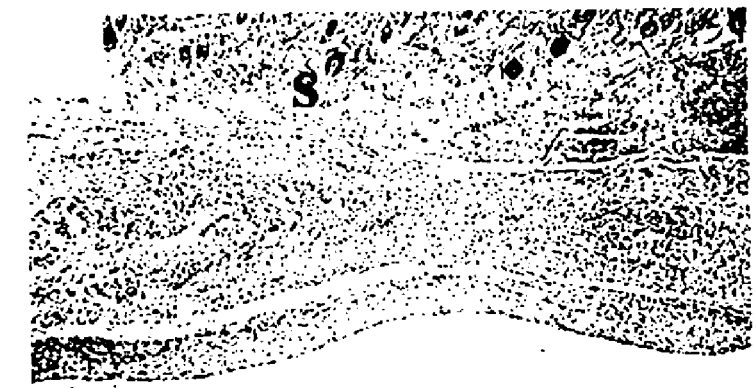

FUNCTIONALIZED DERIVATIVES OF HYALURONIC ACID, FORMATION OF HYDROGELS IN SITU USING SAME, AND METHODS FOR MAKING AND USING SAME

TECHNICAL FIELD OF THE INVENTION

This invention is directed to biomaterials for spatially and temporally controlled delivery of bioactive agents such as drugs, growth factors, cytokines or cells. In particular, this invention teaches versatile methods for chemical crosslinking of high molecular weight hyaluronic acid under physiological conditions in situ, to form polymerizable biodegradable materials. The methods are based on the introduction of functional groups into hyaluronic acid (HA) via formation of an active ester at the carboxylate of the glucuronic acid moiety as an intermediate and subsequent substitution with a side chain containing a nucleophilic group on one end and a (protected) functional group on the other end. The introduced functional groups allow for crosslinking of the HA derivatives. Crosslinked hyaluronic acid hydrogels of this invention are useful in various surgical applications and as a temporary scaffold for tissue regeneration, e.g., in cartilage repair.

BACKGROUND OF THE INVENTION

Repair of Articular Cartilage

The failure of regenerating persistent hyaline cartilage by surgical procedures has prompted investigators to attempt repair using biological strategies. The biological repair of articular cartilage is, with a few exceptions, still at an experimental stage. Biological cartilage repair has been approached in two basic ways. First, autologous chondrocytes have been transplanted into a lesion to induce repair (Grande et al., *J. Orthop. Res.* 7, 208–214 (1989); Brittberg et al., *New Engl. J. Med.* 331, 889–895 (1994); Shortkroff et al., *Biomaterials* 17, 147–154 (1996)). Chondrocytes may be obtained from a low-loaded area of a joint and proliferated in culture (see Grande; Brittberg; Shortkroff, supra), or mesenchymal stem cells may be harvested, e.g., from the iliac crest marrow, and induced to differentiate along the chondrocyte lineage using growth factors (Harada et al., *Bone* 9, 177–183 (1988); Wakitani et al., *J. Bone Joint Surg.* 76-A, 579–592 (1994)). The chondrocyte transplantation procedures currently attempted clinically, although promising, are hampered because technically they are very challenging, the cell preparation is very expensive, and the potential patient pool is limited by age, defect location, history of disease, etc. Cells have also been transplanted into cartilage defects in the form of perichondral grafts, e.g., obtained from costal cartilage, but with limited success due to the limit in donor material and the complication of endochondral ossification of the graft site observed in long-term follow-up (Amiel et al., *Connect. Tissue Res.* 18, 27–39 (1988); O'Driscoll et al., *J. Bone Joint Surg.* 70-A, 595–606 (1988); Homminga et al., *Acta Orthop. Scand.* 326–329 (1989); Homminga et al., *J. Bone Joint Surg.* 72-B, 1003–1007 (1990)). A second approach is aimed at the recruitment of mesenchymal stem cells from the surrounding connective tissue, e.g., synovium, using chemotactic and/or mitogenic factors (Hunziker and Rosenberg, *J. Bone Joint Surg.* 78-A, 721–733 (1996); see also U.S. Pat. No. 5,368,858). The availability of growth factors and cytokines in recombinant form and the lack of complicated cell transplantation make this procedure a very attractive alternative. The shortcoming of both procedures is the difficulty to stably anchor the repair-inducing factors, whether tissue grafts, cells, or growth factors, within the defect site. Also, outlining of the space that is to be repaired, e.g., by filling it with a matrix material, appears to be crucial to recreate a level cartilage surface (Hunziker and Rosenberg, supra). Thus far, the availability of candidate matrix materials has been the limiting factor, and anchoring of materials seeded with chondrocytes and/or chondrogenic factors difficult, explaining the unsatisfactory results obtained with currently available materials such as polylactic acid and polyglycolic acid scaffolds (Freed et al., *J. Biomed. Mat. Res.* 28, 891–899 (1994); Chu et al., *J. Biomed. Mat. Res.* 29, 1147–1154 (1995)); calcium phosphate minerals (Nakahara et al., *Clin. Orthop.* 276, 291–298 (1992)), fibrin sealants (Itay et al., *Clin. Orthop.* 220, 284–303 (1987)), and collagen gels (Wakitani et al., *J Bone Joint Surg.* 71-B, 74–80 (1989)). We have developed novel biodegradable materials based on hyaluronic acid which are optimized for the biological requirements posed on a repair material in a synovial joint and which allow in situ polymerization.

Biology of Hyaluronic Acid and its Therapeutic Use

Hyaluronic acid (HA) is unique among glycosaminoglycans in that it is not covalently bound to a polypeptide. HA is also unique in having a relatively simple structure of repeating nonsulfated disaccharide units composed of D-glucuronic acid (GlcUA) and N-acetyl-D-glucosamine (GlcNAc) (Scott et al., *The Chemistry, Biology and Medical Applications of Hyaluronan and Its Derivatives*, T. C. Laurent (ed.), Portland Press, London, (hereinafter "Hyaluronan and Its Derivatives"), pp. 7–15 (1998)). Its molecular mass is typically several million Daltons. HA is also referred to as hyaluronan or hyaluronate, and exists in several salt forms (see formula I).

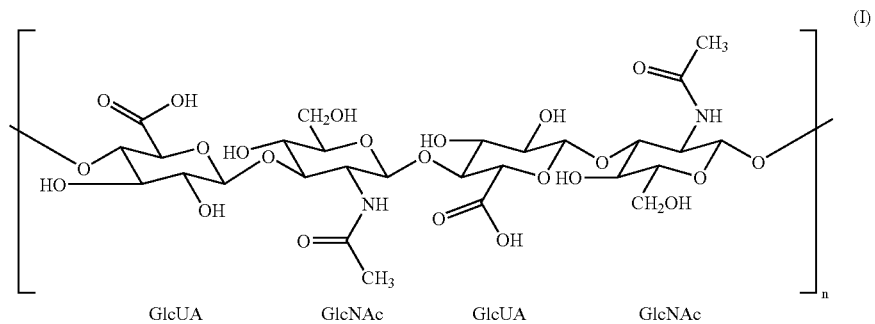

HA is an abundant component of cartilage and plays a key structural role in the organization of the cartilage extracellular matrix as an organizing structure for the assembly of aggrecan, the large cartilage proteoglycan (Laurent and Fraser, *FASEB J.* 6, 2397–2404 (1992); Mörgelin et al., *Biophys. Chem.* 50, 113–128 (1994)). The noncovalent interactions of aggrecan and link protein with HA lead to the assembly of a large number of aggrecan molecules along the HA-chain and mediate retention of aggrecan in the tissue. The highly negatively charged aggrecan/HA assemblies are largely responsible for the viscoelastic properties of cartilage by immobilizing water molecules. A number of cell surface receptors for HA have been described and shown to play a critical role in the assembly of the pericellular matrix of chondrocytes and other cells, e.g., isoforms of CD44 and vertebrate homologues of Cdc37 (Knudson and Knudson, *FASEB J.* 7, 1233–1241 (1993); Grammatikakis et al., *J. Biol. Chem.* 270, 16198–16205 (1995)), or to be involved in receptor-mediated endocytosis and degradation of HA to control HA levels in tissues and body fluids (Laurent and Fraser, supra; Fraser et al., *Hyaluronan and Its Derivatives*, pp. 85–92 (1998)). Blocking of the interaction of these receptors with HA in prechondrogenic micromass cultures from embryonic limb bud mesoderm inhibits chondrogenesis, indicating that the establishment and maintainance of a differentiated chondrocyte phenotype is at least in part dependent on HA and HA-receptor interactions (Maleski and Knudson, *Exp. Cell. Res.* 225, 55–66 (1996)).

HA and its salts are currently being used in therapy for arthropathies by intraarticular injection (Strachnan et al., *Ann. Rheum. Dis.* 49, 949–952 (1990); Adams, *Hyaluronan and Its Derivatives*, pp. 243–253 (1998)), in opthalmic surgery for intraocular lens implantation (Denlinger, *Hyaluronan and Its Derivatives*, pp. 235–242 (1998), to promote wound healing in various tissues (King et al., *Surgery* 109, 76–84 (1991)), or more recently, in derivatized and/or crosslinked form to manufacture thin films which are used for tissue separation (for review see Laurent and Fraser, supra; Weiss, *Hyaluronan and Its Derivatives*, pp. 255–266 (1998); Larsen, *Hyaluronan and Its Derivatives*, pp. 267–281 (1998); Band, *Hyaluronan and Its Derivatives*, pp. 33–42 (1998)). Extensive efforts have been made by various laboratories to produce derivatives of HA with unique properties for specific biomedical applications. Most of the developments have been focusing on the production of materials such as films or sponges for implantation and the substitution of HA with therapeutic agents for delayed release and/or prolonged effect (for review see Band, supra; Prestwich et al., *Hyaluronan and Its Derivatives*, pp. 43–65 (1998); Gustafson, *Hyaluronan and Its Derivatives*, pp. 291–304 (1998)). Strategies have included esterification of HA (U.S. Pat. Nos. 4,957,744 and 5,336,767), acrylation of HA (U.S. Pat. No. 5,410,016), and cross-linking of HA using divinyl sulfone (U.S. Pat. No. 4,582,865) or glycidyl ether (U.S. Pat. No. 4,713,448). However, the modified HA molecules show altered physical characteristics such as decreased solubility in water and/or the chemical reaction strategies used are not designed for crosslinking of HA under physiological conditions (in an aqueous environment, at pH 6.5–8.0). It is well known that polyaldehydes can be generated by oxidizing sugars using periodate (Wong, CRC Press, Inc., Boca Rayton, Fla., pp. 27 (1993); European Patent No. 9615888). Periodate treatment oxidizes the proximal hydroxyl groups (at C2 and C3 carbons of glucuronic acid moiety) to aldehydes thereby opening the sugar ring to form a linear chain (Scheme 1). While periodate oxidation allows for the formation of a large number of functional groups, the disadvantage is the loss of the native backbone structure. Consequently, the generated derivative may not be recognized as HA by cells. In fact, hydrogels formed by using periodate oxidized HA as a crosslinker, e.g., in combination with the HA-amines described herein, showed very limited tissue transformation and poor cellular infiltration in the rat ectopic bone formation model (FIG. 6). This is in sharp contrast to the HA-aldehyde derivatives described herein.

The introduction of free amino groups on HA, which could be used for further convenient coupling reactions under mild physiological conditions, has been a subject of great interest. Previous methods have produced a free amino group on high molecular weight HA by alkaline N-deacetylation of its glucosamine moiety (Curvall et al., *Carbohvdr. Res.* 41, 235–239 (1975); Dahl et al., *Anal. Biochem.* 175, 397–407 (1988)). However, concomitant degradations of HA via beta-elimination in the glucuronic acid moiety was observed under the harsh reaction conditions needed. This is of particular concern because low molecular weight HA fragments, in contrast to high molecular weight HA, have been shown to be capable of provoking inflammatory responses (Noble et al., *Hyaluronan and Its Derivatives*, pp. 219–225 (1998)). An early report claimed that carbodiimide-catalyzed reaction of HA with glycine methyl ester, a monofunctional amine, led to the formation of an amide linkage (Danishefsky and Siskovic, *Carbohydr. Res.* 16, 199–201 (1971)). This however, has been proven by a number of studies not to be the case (Kuo et al., *Bioconjugate Chem.* 2, 232–241 (1991); Ogamo et al., *Carbohvdr. Res.* 105, 69–85 (1982)). Under mildly acidic conditions the unstable intermediate O-acylisourea is readily formed, which in the absence of nucleophiles, rearranges by a cyclic electronic displacement to a stable N-acylurea (Kurzer and Douraghi-Zedeh, *Chem. Rev.* 67, 107–152 (1967)). This O→N migration of the O-acylisourea also occurs when the nucleophile is a primary amine (Kuo et al., supra) and any amide formation that does occur is insignificant as reported by Ogamo et al., supra. Experiments where high molecular weight HA (Mr~2×10$^6$ Da) was reacted with an excess of the fluorescent label 5-aminofluorescine in the presence of the carbodiimide EDC achieved only 0.86% of theoretical labelling. The introduction of a terminal hydrazido group on HA with a variable spacer has recently been achieved and has led to the ability to conduct further coupling and crosslinking reactions (Pouyani and Prestwich, *Bioconjugate Chem.* 5, 339–347 (1994), U.S. Pat. Nos. 5,616,568, 5,652,347, and 5,502,081; Vercruysse et al., *Bioconjugate Chem.* 8, 686–694 (1997)).

It is an objective of this invention to provide a method for more versatile modification of HA with various functional groups that allow for crosslinking of the HA derivatives under physiological conditions. It is another objective that the method of functionalization does not compromise the molecular weight or chemical identity (except of the target carboxyl group for coupling) of HA. It is a further objective that the method of functionalization provides HA molecules that are well tolerated in vivo and are biodegradable.

It is also an objective of this invention to identify HA derivatives and methodology for in situ polymerization thereof to provide a biodegradable scaffold for tissue regeneration. It is another objective that the HA materials can be polymerized in the presence of cells to serve as a vehicle for cell transplantation. It is a further objective to provide methodology for functionalization and cross-linking of HA that allows for variations in the biomechanical properties of the formed gels as well as in the sensitivity to cellular infiltration and degradation.

SUMMARY OF THE INVENTION

Biomaterials for spatially and temporally controlled delivery of bioactive agents such as drugs, growth factors, cytokines or cells, are a key factor for tissue repair. In particular, in situ polymerizable biodegradable materials are needed for cartilage resurfacing that are designed to withstand the mechanical forces in a joint. We have developed a versatile method for chemical crosslinking of high molecular weight hyaluronic acid under physiological conditions. The method is based on the introduction of functional groups into hyaluronic acid by formation of an active ester at the carboxylate of the glucuronic acid moiety and subsequent substitution with a side chain containing a nucleophilic group on one end and a (protected) functional group on the other end. We have formed hyaluronic acid with amino or aldehyde functionality, and formed hydrogels with modified hyaluronic acid and bifunctional crosslinkers or mixtures of hyaluronic acid carrying different functionalities using active ester- or aldehyde-mediated reactions. Physical and chemical properties of the hydrogels of this invention were evaluated using biomechanical testing, and by assaying sensitivity towards degradation by glycosidases such as testicular hyaluronidase. Biocompatibility was evaluated using cell culture assays and subcutaneous implantation of the hyaluronic acid materials in rats. This in vivo assay is also the established model for induction of ectopic bone formation by members of the transforming growth factor β family (TGF-β), and several crosslinked hyaluronic acid materials of this invention gave excellent ectopic bone formation in vivo when loaded with appropriate growth factor(s).

As set forth below in the detailed description of the invention, the compositions of the invention have many therapeutic uses. For example, compositions of the invention may be used to stem hemorrhage in general surgery, reconstruct nerves and vessels in reconstructive, neuro- and plastic surgery, and to anchor skin, vascular, or cartilage transplants or grafts in orthopedic, vascular, and plastic surgery. Compositions of the invention are also useful as vehicles for the delivery of cells or bioactive molecules such as growth factors to stimulate focal repair. Local delivery of growth factors facilitates wound healing and tissue regeneration in many situations, not only in promoting bone formation and stimulating cartilage repair in orthopedic procedures, but also, e.g., in treating pathological wound conditions such as chronic ulcers. These compositions may also serve as a scaffold to generate artificial tissues through proliferation of autologous cells in culture. On the other hand, the anti-adhesive property of some compositions with respect to cells render such compositions particularly suitable to generate tissue separations and to prevent adhesions following surgery. The viscoelastic properties of HA make it particularly well suited for this purpose, and it is used clinically to achieve temporal pain relief by repeated intraarticular injections in arthropathies as a "joint lubricant", as a protective agent for eye irritations and in ophthalmic surgery, as a barrier to cells in facial and other reconstructions in plastic surgery and dentistry, in reconstructive surgery of tendons, in surgical procedures in the urogenital system, and in thoracic surgery. The injectable nature of the compositions of the invention also renders them suitable for tissue augmentation in plastic surgery, where the HA matrix serves primarily as an inert biocompatible filler material (Balasz and Laurent, *Hyaluronan and Its Derivatives*, pp. 325–326 (1998)), e.g., for filling dermal creases or lip reconstruction.

HA hydrogels match several of the desired properties for a biodegradable material biocompatible with cells. The relatively simple repetitive structure of HA allows for specific modification and introduction of a large number of functional groups, for crosslinking to generate hydrogels with excellent physical proprties. HA hydrogels have also successfully been used as a delivery vehicle in chondrocyte transplantation studies (Robinson et al., *Calcif Tissue Int.* 46, 246–253 (1990)) and HA has proven its biocompatibility in various forms in clinical practice (for review see Laurent and Fraser, supra; Balazs and Laurent, supra).

The reaction mechanisms we have explored for in situ polymerization of HA derivatives are compatible with an aqueous environment and are non-toxic to cells. The aldehyde-mediated crosslinking strategies follow reactions occurring physiologically in crosslinking of fibrillar collagens and elastin. NHS-esters provide an alternative for rapid formation of stable bonds under physiological conditions, primarily by reaction with primary amines. The technology of NHS-ester-mediated protein crosslinking has been developed for materials with applications in plastic surgery that require in situ polymerization (U.S. Pat. No. 5,413,791)).

BRIEF DESCRIPTION OF THE DRAWINGS

FIG. 4 shows digestion of crosslinked HA hydrogels with hyaluronidase.

FIG. 5 shows phase contrast images of cells cultured on different crosslinked HA hydrogels.

FIG. 7 shows in vivo evaluation of HA hydrogels crosslinked with different NHS-esters. Subcutaneous implantation in rats of HA hydrogels consisting of (FIG. 7A) 12 mg/ml highly modified (~65–70%) HA-amine (adipic dihydrazido-HA) crosslinked with 15 mg/ml $(SPA)_2$-PEG, (FIG. 7B) 12 mg/ml optimally modified (~20–25%) HA-amine (adipic dihydrazido-HA) crosslinked with 15 mg/ml $SPA_2$-PEG, or (FIG. 7C) 12 mg/ml of the same optimally modified HA-amine crosslinked with 3 mg/ml DTSSP (crosslinker concentrations are equal on a molar basis). The hydrogels also contained 1 mg/ml prefibrillized intact collagen type I, 200 μg/ml BMP-2 and 50 ng/ml TGF-β2 to induce bone formation. Tissue specimens were harvested 10 days post implantation, fixed in formalin and processed for histology by paraffin embedding. Sections were stained with Haematoxylin/Eosin. m, matrix material (note: matrix material shrinks during dehydration); s, skin (indicates orientation of implant).

BRIEF DESCRIPTION OF THE REACTION SCHEMES

Scheme 1 illustrates periodate oxidation of hyaluronic acid.

Scheme 2 illustrates coupling of amines to hyaluronic acid with EDC via an active triazole ester intermediate.

Scheme 3 illustrates coupling of amines to hyaluronic acid with EDC via an active N-hydroxysuccinimde ester intermediate.

Scheme 4 illustrates crosslinking of amine functionalized hyaluronic acid with various bifunctional N-hydroxysuccinimde ester crosslinkers to form hydrogels. (1. $(SPA)_2$-PEG; 2. DTSSP).

Scheme 5 illustrates crosslinking of amine functionalized hyaluronic acid with glutaraldehyde to form hydrogels. In addition to the conventional reaction of aldehydes with amines that results in the formation of a Schiff base, glutaraldehyde is also known to undergo polymerization by aldol condensation yielding polymers with α,β-unsaturated aldehydes at neutral or slightly alkaline pH (Richards and Knowles, *J. Mol. Biol.* 37, 231–233 (1968)). Subsequent, nucleophilic addition of amines at the ethylenyl double bond creates a stable crosslink.

Scheme 6 illustrates formation of hydrogels with aldehyde functionalized hyaluronic acid. (1. amine functionalized HA; 2. bifunctional amine)

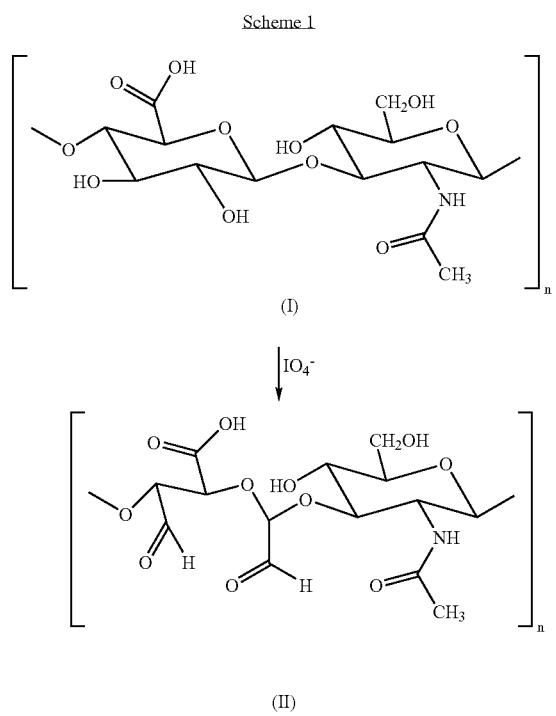

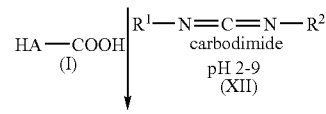

-continued
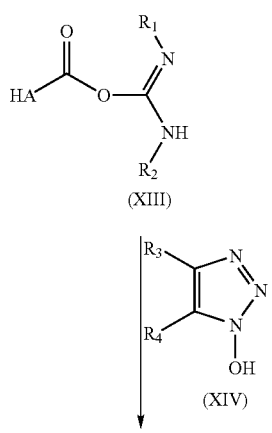
Scheme 3
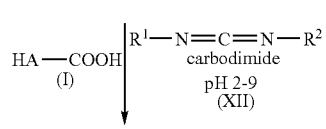
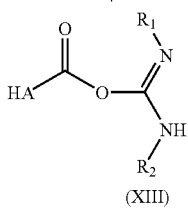
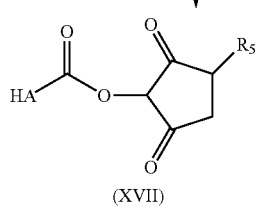
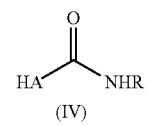
Scheme 4
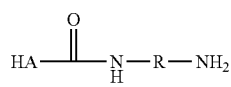
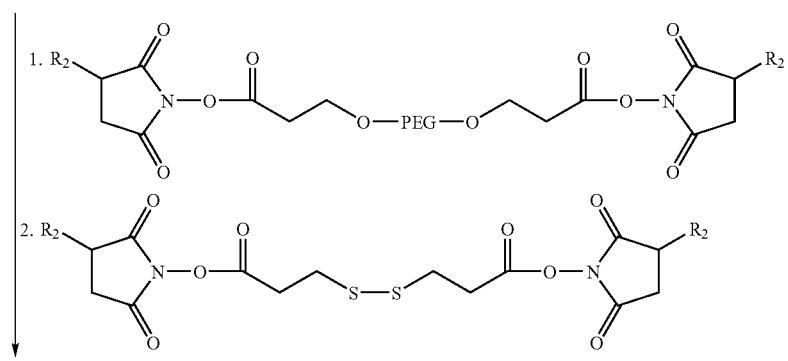

-continued

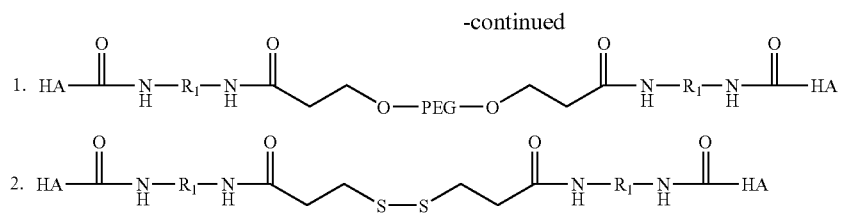

Scheme 5

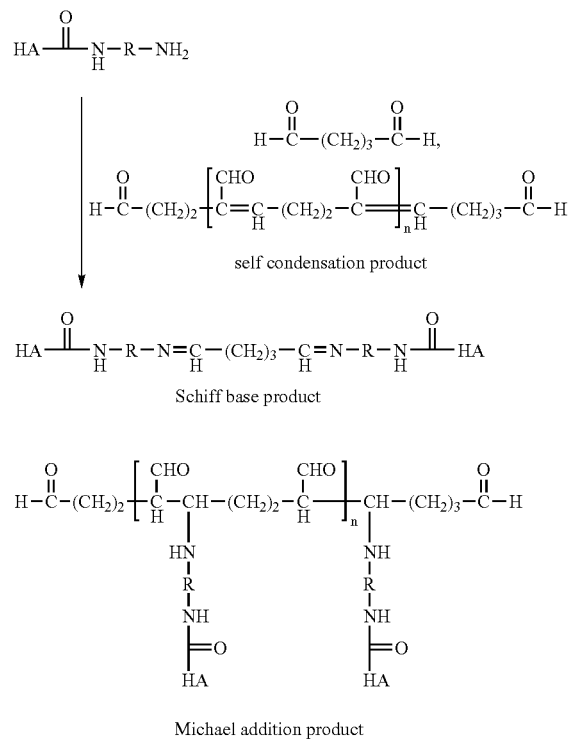

Scheme 6

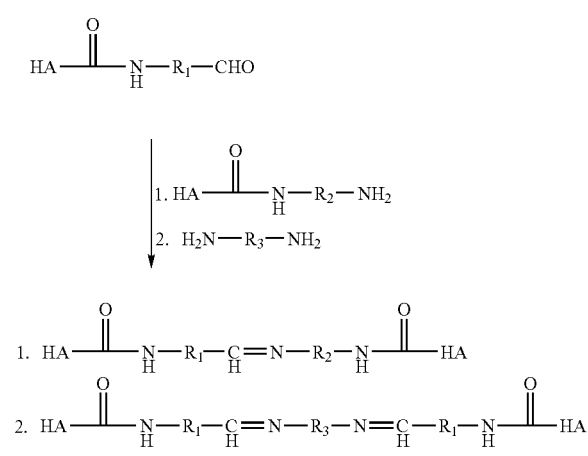

DETAILED DESCRIPTION OF THE INVENTION

Using the methods of our invention, we generate an activated form of HA that differs minimally from native HA to conserve its unique physico-chemical properties. We also effect a minimal change affecting only a relatively small number of dissacharide units of native HA so that we do not alter its property to serve as a cell substratum.

We initially attempted to generate an aldehyde derivative of HA by reduction of the carboxyl groups of the glucuronic acid moieties into aldehydes using 9-borabicyclo-3,3-nonane, a method that allows direct conversion of the carboxylic acid into the aldehyde (Cha et al., *Bull. Korean Chem. Soc.* 9, 48–52 (1988), Cha et al., *Org. Prep. Proc. Int.* 21, 451–477 (1989)):

$$\text{HA—COOH(I)} \longrightarrow \text{HA—CHO} \tag{II}$$

Figure 1:
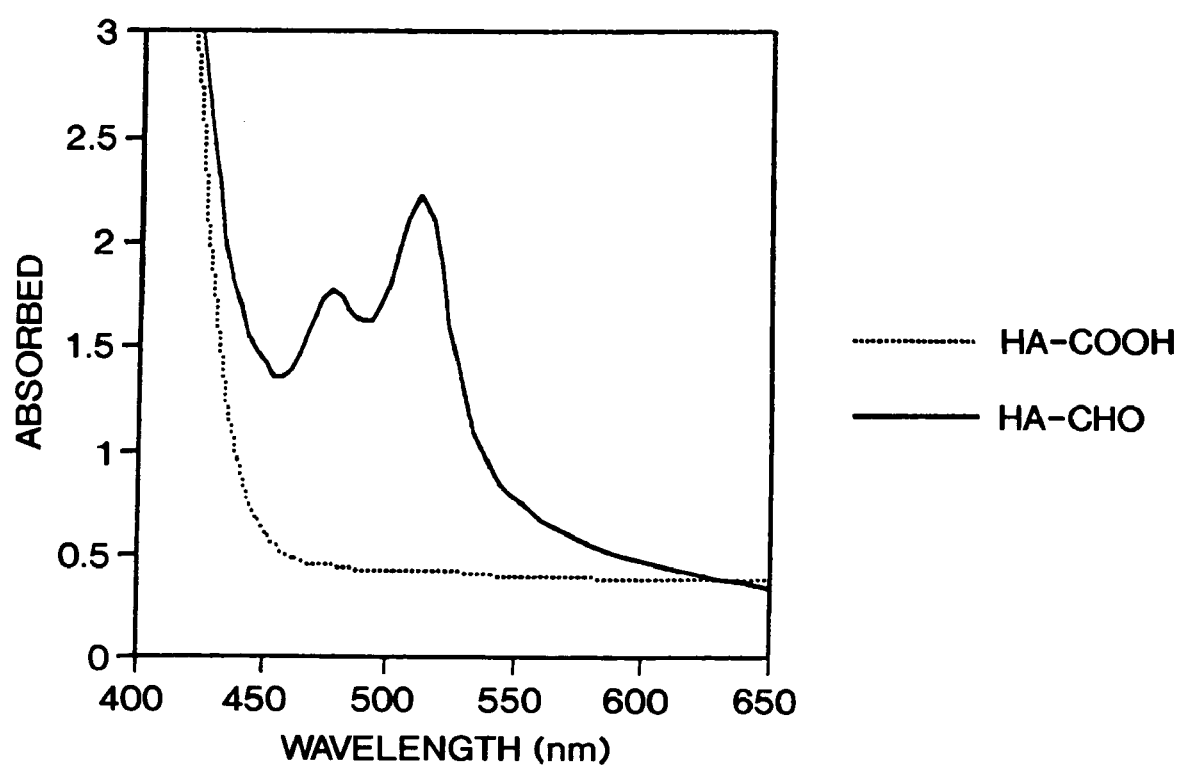
FIG. 1 shows the results of a ninhydrin test after reductive alkylation of HA and HA-aldehyde in the presence of putrescine. Reductive alkylation was carried out with an excess of putrescine in the presence of pyridine borane. HA or derivatives thereof were purified by repeated ethanol precipitation prior to detection of free amino groups on the HA chain by using the ninhydrin test (Sheng et al., *Anal. Biochem.* 211, 242–249 (1993)).

However, even though preliminary testing indicated the conversion of the carboxyl groups into aldehydes to a degree of approximately 5–10% (FIG. 1), mixtures of concentrated, viscous HA-aldehyde solutions (~10 mg/ml) with 'small' polyamines such as putrescine, lysine, polylysine, histidine, or polyhistidine did not generate stable gels in a reasonable time frame to be suitable for in situ polymerization. It is important to note that the chemical properties of HA are determined not merely by its functional groups per se but also by the accessibility of these functional groups of HA in an aqueous environment, which is related to the overall conformational structure and Theological properties of HA. HA behaves like a hydrogel in an aqueous media even in the absence of crosslinks because it forms a network stabilized by hydrogen bonds and van der Waals forces (Laurent and Fraser, supra). To increase the accessibility of functional groups, we introduced a spacer between the functional group and the HA chain.

Introducing a Functionalized Side Chain onto HA

We subsequently developed methodology for introducing side chains into HA by carbodiimide-mediated coupling of primary or secondary amines to the carboxyl group of the glucuronic acid moiety using an active ester intermediate. We have used this methodology to generate HA with different terminal functional groups for crosslinking including acetals, aldehydes, amines, and hydrazides. A wide range of functionalized amines are commercially available which allows us to introduce a wide variety of different functional groups useful for crosslinking under physiological conditions using this methodology, including maleimides that react specifically with sulfhydryls or arylazides for photo-crosslinking besides the amines and aldehydes described below.

Direct carbodiimide-mediated coupling of amines to the carboxyl group of HA in an aqueous environment, e.g., with EDC (1-ethyl-3-[3-dimethylaminopropyl] carbodimide), does not yield the predicted product since the O-acyl isourea that is formed as a reactive intermediate rearranges rapidly to a stable N-acyl urea (Kuo et al., supra). We have demonstrated that by "rescuing" the active O-acyl isourea by formation of a more hydrolysis resistant and non-rearrangable active ester intermediate, the coupling of primary amines to HA is possible. A wide variety of active carboxylic esters exist and could be formed for further reaction including NHS-esters, nitrophenol esters, triazole esters, sulfonic esters, etc., as long as the reagent for their preparation is soluble in H$_2$O or in other polar solvents such as dimethylsulfoxide or dimethylformamide. HA is soluble in H$_2$O or other aprotic polar solvents in native form and when prepared as a sodium salt or when prepared as a tetrabutylammonium salt as described in U.S. Pat. No. 4,957,744, respectively. We have formed active esters of HA with 1-hydroxybenzotriazole (HOBT) or N-hydroxysulfo-succinimide using the H$_2$O soluble carbodiimide EDC for coupling. Nucleophilic additon to the ester formed from HOBT requires the amine to be presented in unprotonated form at acidic pH (about 5.5 to 7.0). Only a limited number of amines including hydrazines and activated amines, e.g., ethylene diamine, have pKa values in a suitable range and are consequently unprotonated and reactive with the ester-intermediate formed with HOBT (Scheme 2). Simple primary amines, e.g., putrescine, which typically have pKa values >9 do not form significant amounts of adduct under acidic coupling conditions. The N-hydroxysulfosuccinimide-derived intermediate allows for the coupling reaction to be carried out at neutral pH (about 7.0 to 8.5) and consequently yields products by reaction with simple primary amines (Scheme 3).

Consequently, this methodology allows for the following reactions to be carried out:

HA—COOH(I)+H$_2$N—R(III)------>HA-CO—NH—R  (IV)

HA—COOH(I)+R'—NH—R(V)------>HA-CO—NR'—R  (VI)

wherein R and R' are alkyl, aryl, alkylaryl or arylalkyl side chains which may contain hetero atoms such as oxygen, nitrogen, and sulfur. The side chain may be branched or unbranched, and be saturated or may contain one or more multiple bonds. The carbon atoms of the side chain may be continuous or may be separated by one or more functional groups such as an oxygen atom, a keto group, an amino group, an oxycarbonyl group, etc. The side chain may be substituted with aryl moieties or halogen atoms, or may in whole or in part be formed by ring structures such as cyclopentyl, cyclohexyl, cycloheptyl, etc. The side chain may have a terminal functional group for crosslinking such as aldehyde, amine, arylazide, hydrazide, maleimide, sulfhydryl, etc. The side chain may be a bioactive peptide, e.g., containing receptor binding sites, crosslinking sites for transglutaminases, or proteolytic cleavage sites.

Terminal functional groups of the side chain useful for crosslinking of HA under physiological conditions may be selected from the following list:

1. aldehydes, see Examples

H$_2$N—R—CHO  (VII)

2. amines, see Examples

H$_2$N—R—NH$_2$  (VIII)

3. arylazides, e.g., 4-(p-azidosalicylamido)butylamine

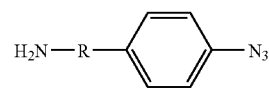
(IX)

4. maleimides, e.g., 4-(N-maleimidomethyl)cyclohexane-1-carboxylhydrazide

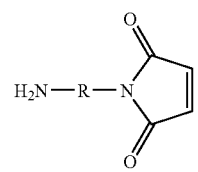
(X)

5. sulfhydryls, e.g., S-methylsulfide cysteine

H$_2$N—R—SH  (XI)

6. peptides, e.g., H$_2$N-APQQEA, comprising substrate sites for enzymatic crosslinking, e.g., by transglutaminases (Parameswaran et al., *Proc. Natl. Acad. Sci. U.S.A.* 87, 8472–8475 (1990); Hohenadl et al., *J. Biol. Chem.* 270, 23415–23420 (1995)).

The carbodiimides useful in this reaction may be represented by the following formula:

R—N=C=N—R'  (XII)

wherein R and R' comprise side chains of variable structure as described above in detail. Carbodiimides which are soluble in an aqueous media are preferred.

The active ester may be of the following class and be formed by carbodiimide-mediated coupling of a compound for preparation of these active esters known to a person in the art:

1. triazole esters, e.g. 1-hydroxybenzotriazole

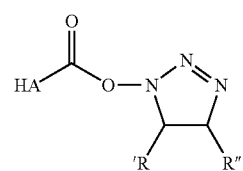
(XIII)

2. NHS-esters, e.g. N-hydroxysulfosuccinimide

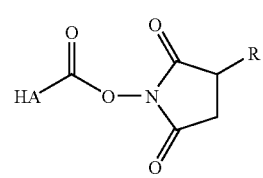
(XIV)

3. nitrophenol esters, e.g. p-nitrophenol

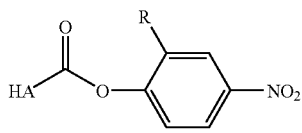
(XV)

Preparation of HA-Aldehyde Derivatives

Figure 2A:
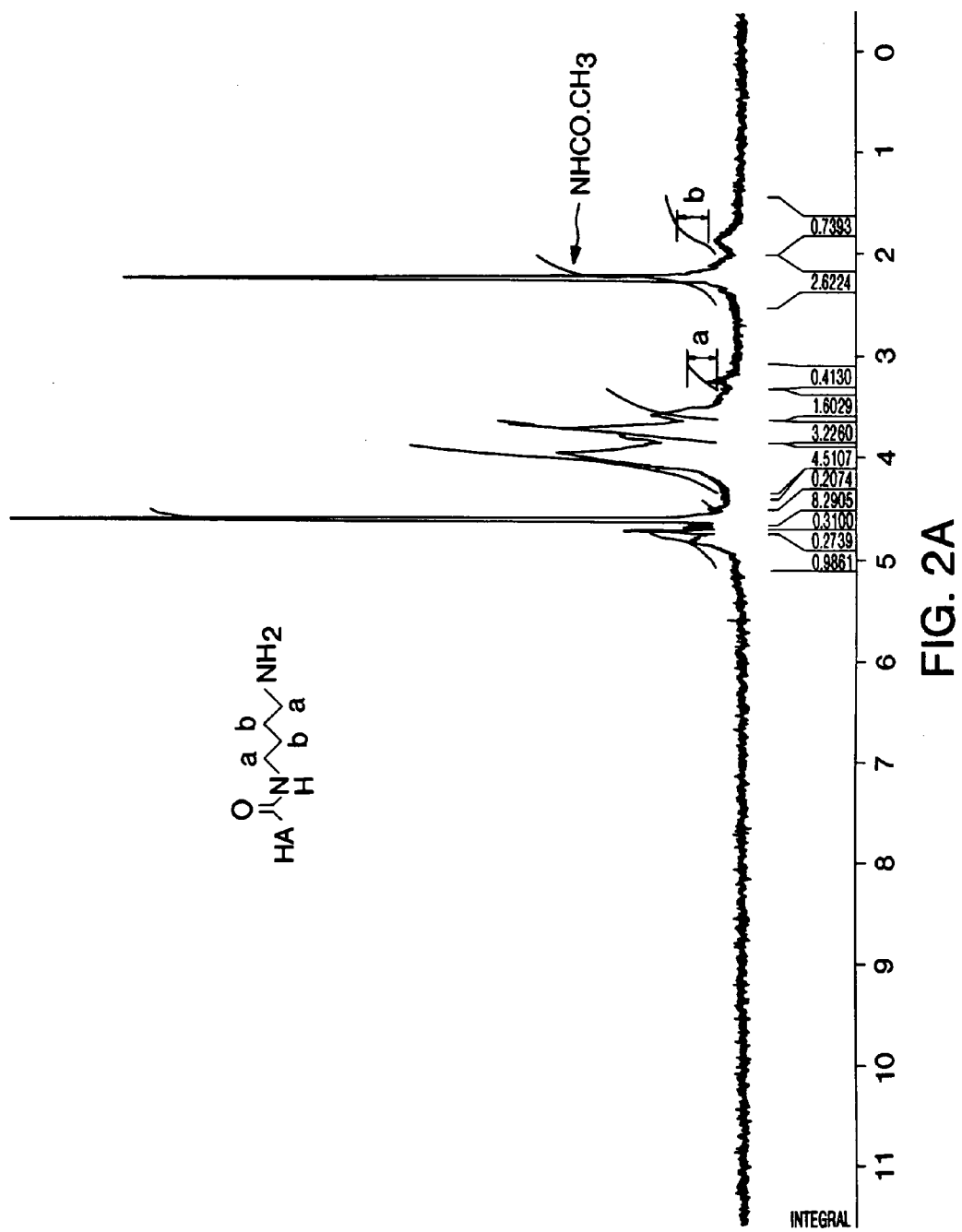
FIG. 2 shows $^1$H NMR of native HA (FIG. 2A) and an HA-derivative with protected aldehyde functionality (FIG. 2B) in $D_2O$ at 300 Mhz. Peaks are assigned as indicated on the structural formula.
Figure 2B:
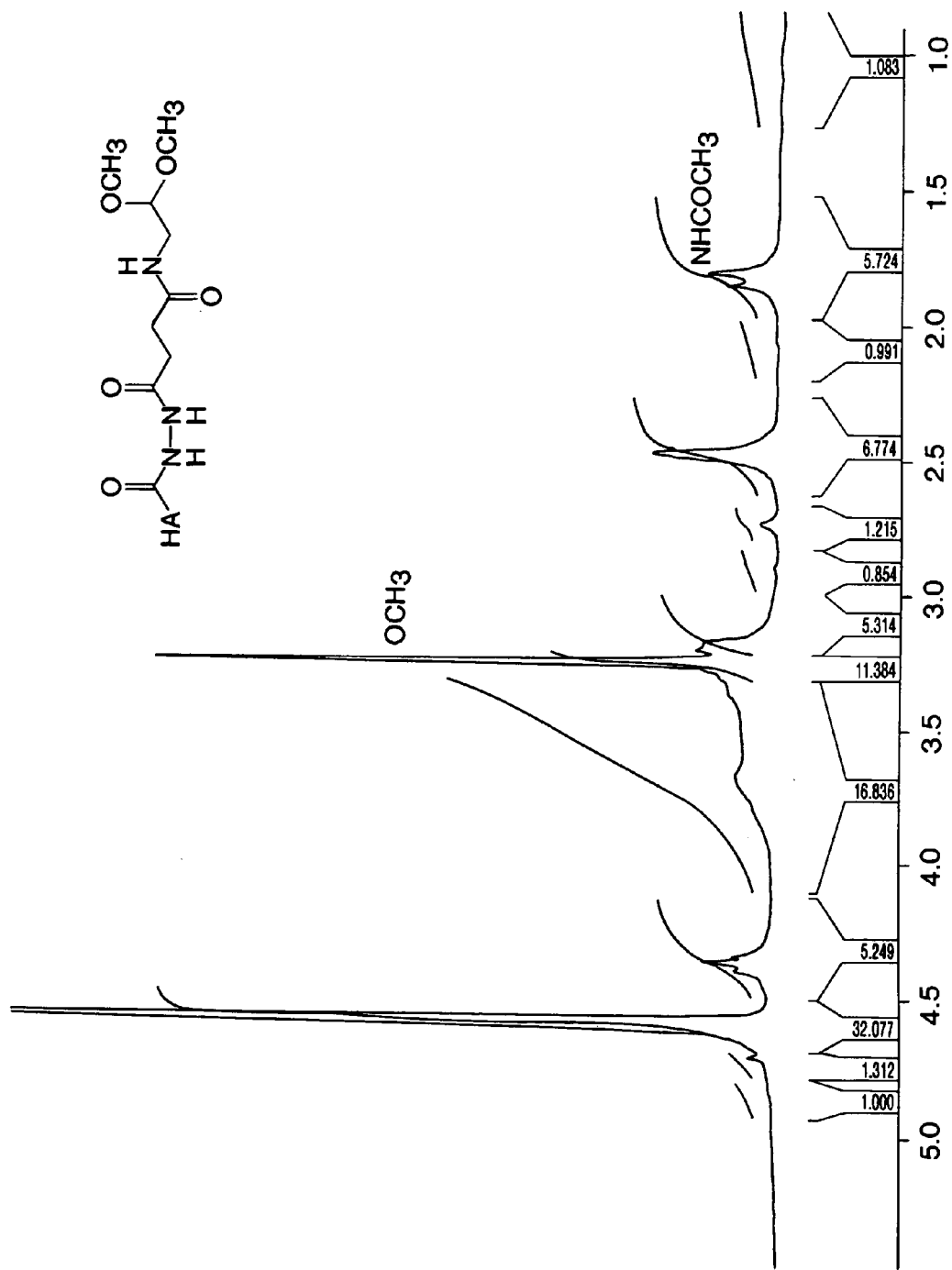
Figure 3A:
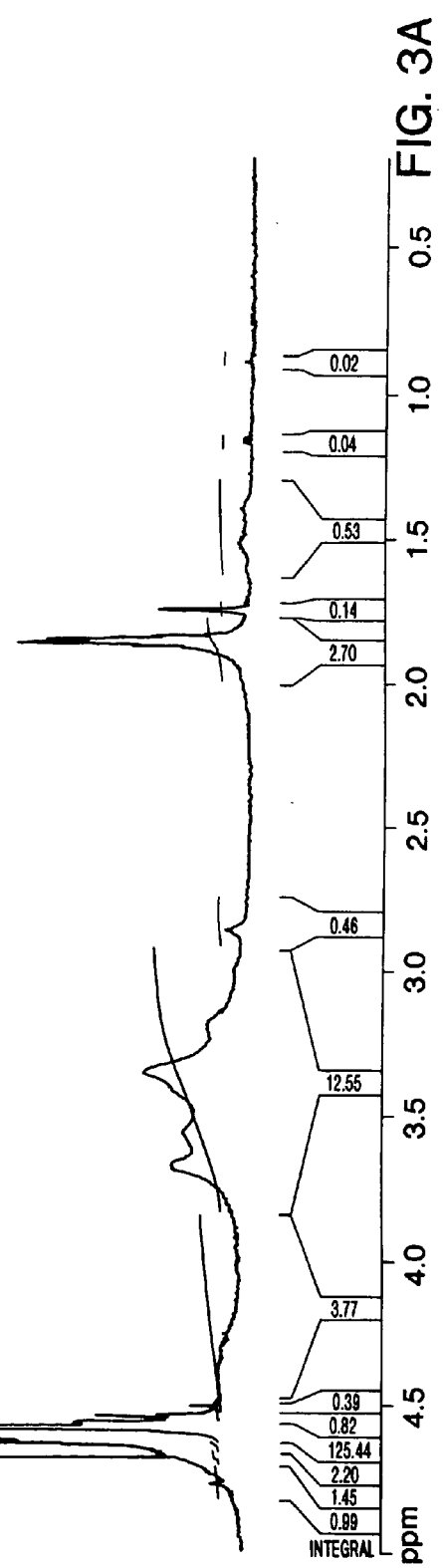
FIG. 3 shows $^1$H NMR of HA-derivatives with amine functionality formed from putrescine (FIG. 3A), histidine (FIG. 3B), lysine (FIG. 3C), and adipic dihydrazide (FIG. 3D) in $D_2O$ at 300 Mhz. Peaks are assigned as indicated on the structural formula.
Figure 3B:
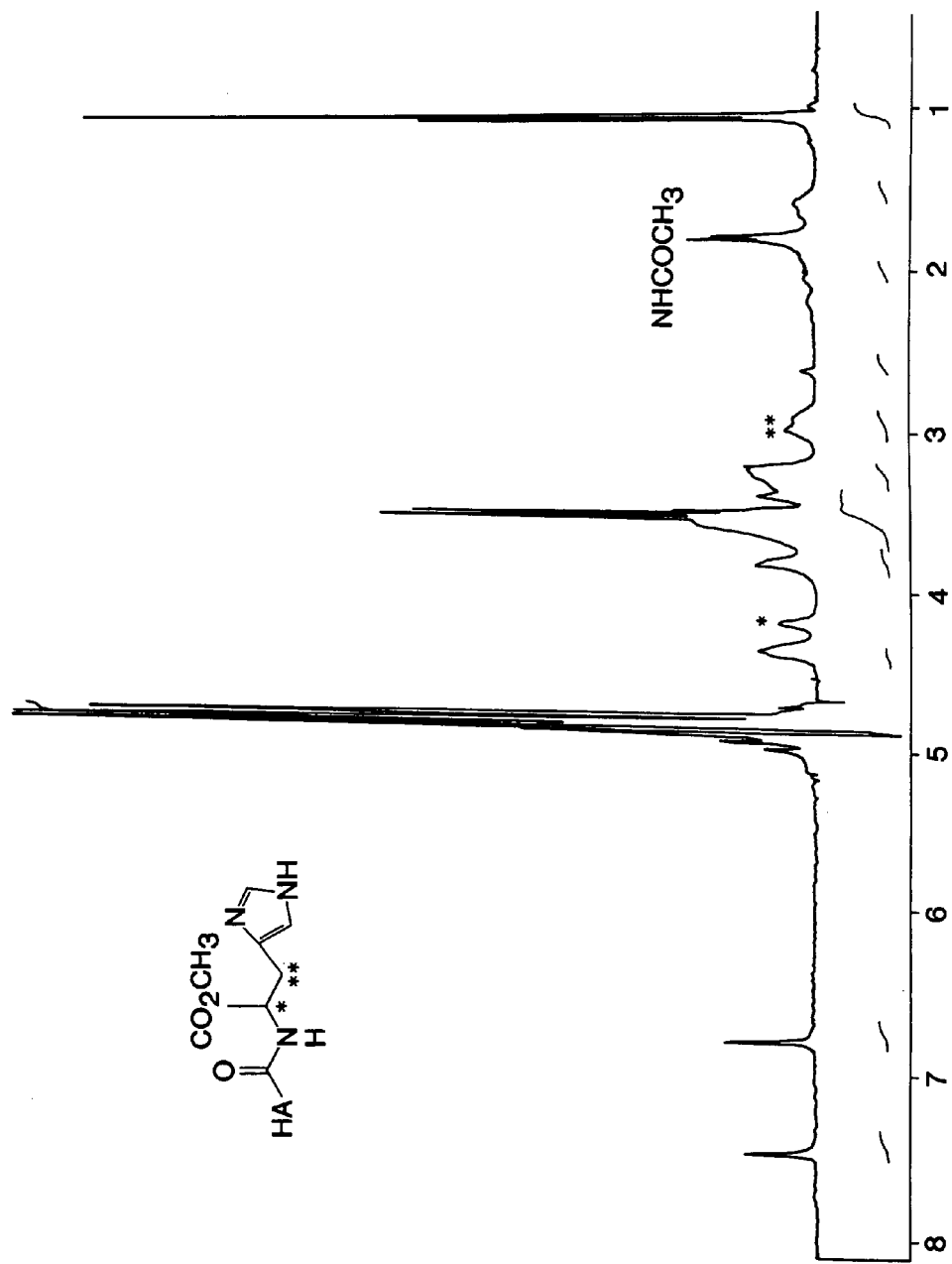
Figure 3C:
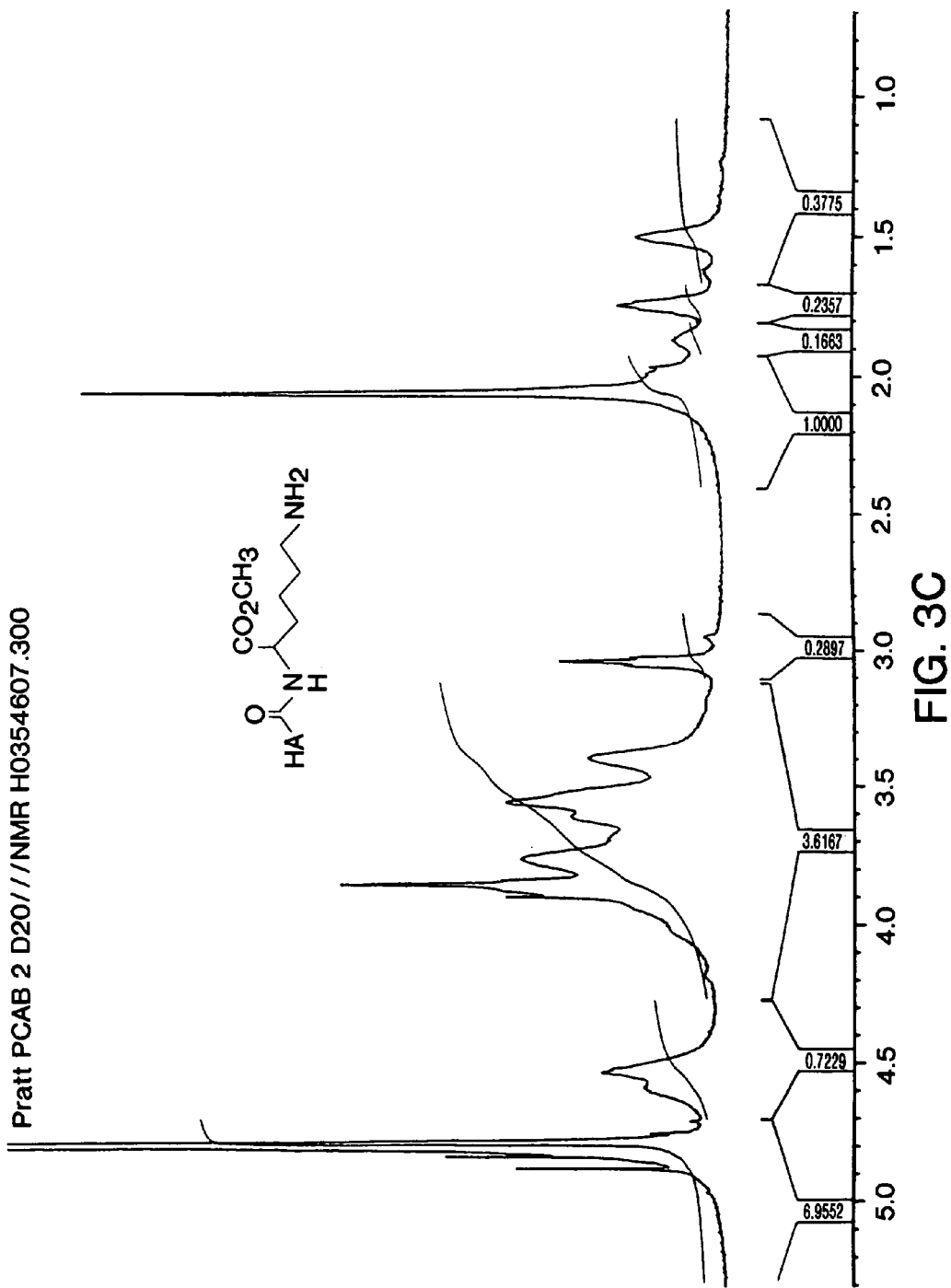
Figure 3D:
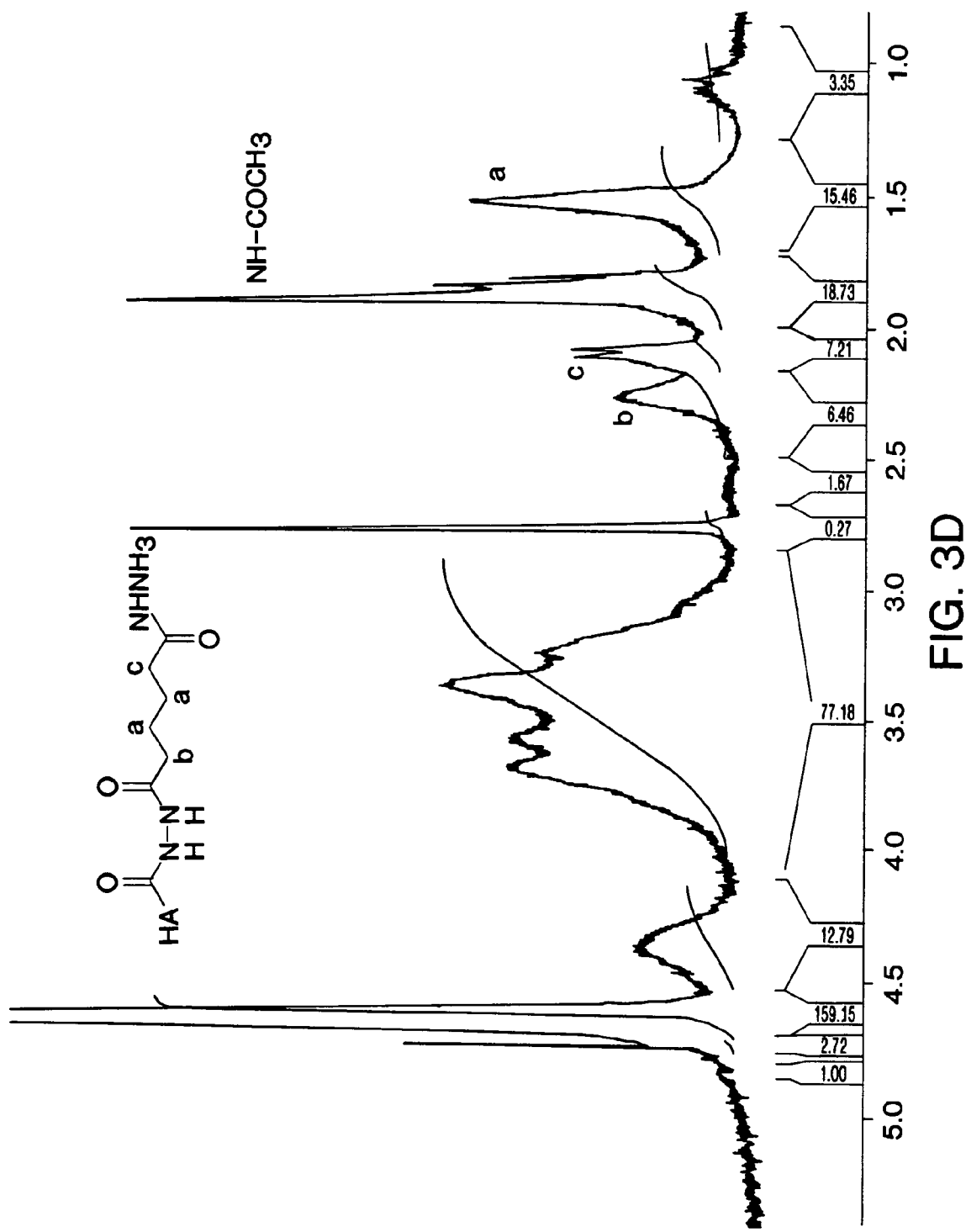

A side chain containing a protected aldehyde in the form of an acetal was prepared as follows. N-(2,2-dimethoxyethyl)-4-(methoxycarbonyl)butanamide was obtained from aminoacet-aldehyde dimethyl acetal and mono-methyl succinate using EDC coupling. An amino group for the coupling to HA was subsequently introduced by reacting the product with hydrazine, yielding the desired side chain with the protected aldehyde, N-(2,2-dimethoxyethyl)-4-(hydrazido)butanamide. The side chain was coupled to HA using HOBT and EDC (Scheme 2). An acetal side chain with a simple primary amine, 1-aminoethyl-dimethylacetal, was conjugated to HA using N-hydroxysuccinimide and EDC (Scheme 3). The HA-derivatives were purified by ethanol precipitation. The nature of the HA-derivatives was confirmed by $^1$H NMR (FIG. 2). The HA-acetal derivatives are easily activated to the reactive aldehydes by mild acid treatment. Other HA-aldehyde derivatives with variations in the length of the side chain have been prepared in a similar manner. See Examples 1–3.

Preparation of HA-amine Derivatives

Diaminoethane, lysine methyl ester, histidine, and adipic, succinic or suberic dihydrazide was coupled to HA using HOBT and EDC (up to 5-fold excess depending on the desired degree of modification) and adjusting the pH to ~6.5 by repeated addition of 0.1M HCl during the reaction (Scheme 2). HA-derivatives were also prepared in a similar manner using N-hydroxysulfosuccinimide and primary amines containing unconjugated amino groups with a higher pKa (>9) such as 1,4-diaminobutane or 1,6 diaminohexane (Scheme 3). The HA derivatives were purified by repeated ethanol precipitation and by extensive dialysis, and the nature of the HA derivatives was confirmed by $^1$H NMR (FIG. 3). The degree of modification was calculated from the NMR data and found to be as high as 70%. Reaction conditions were subsequently adjusted such that a degree of modification of approximately 20% was achieved. Limiting the amount of carbodiimide proved to be most successful in controlling the degree of modification. A degree of modification of 10–25% yielded efficient crosslinking but also a molecule that would still be recognized by glycosidases and by HA receptors as HA and thus allow for recognition and processing of the material by cells (see below). Similar HA derivatives were synthesized using succinic, adipic or suberic dihydrazide or diaminoethane, -butane, or -hexane to study the effect of the length of the spacer separating the introduced functional group from the HA-chain on the subsequent crosslinking. See Examples 4–8.

Crosslinked HA Hydrogels

The functionalized HA molecules can be crosslinked by reacting HA derivatives with different functionalities or using homo- or heterobifunctional crosslinkers which are available in large variety. The following basic reaction schemes are suitable for crosslinking of the described forms of modified HA (see Examples 9–12):

1: aldehyde-mediated crosslinking

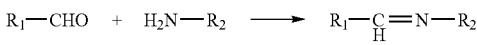

2. active ester-mediated crosslinking

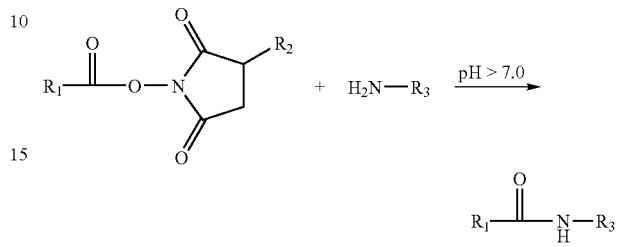

3. maleimide-mediated cros slinking

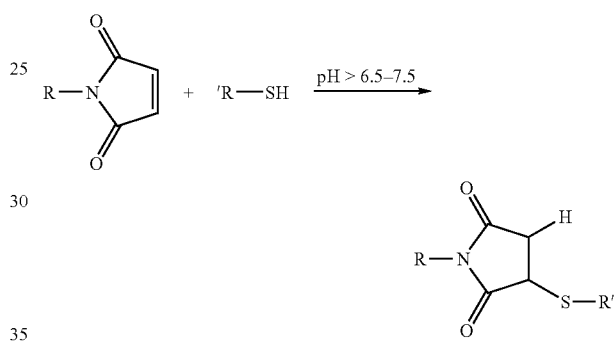

4. photo-crosslinking

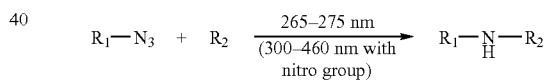

5. enzymatic crosslinking (transglutaminase)

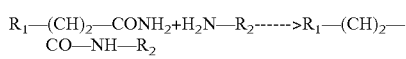

Figure 4A:
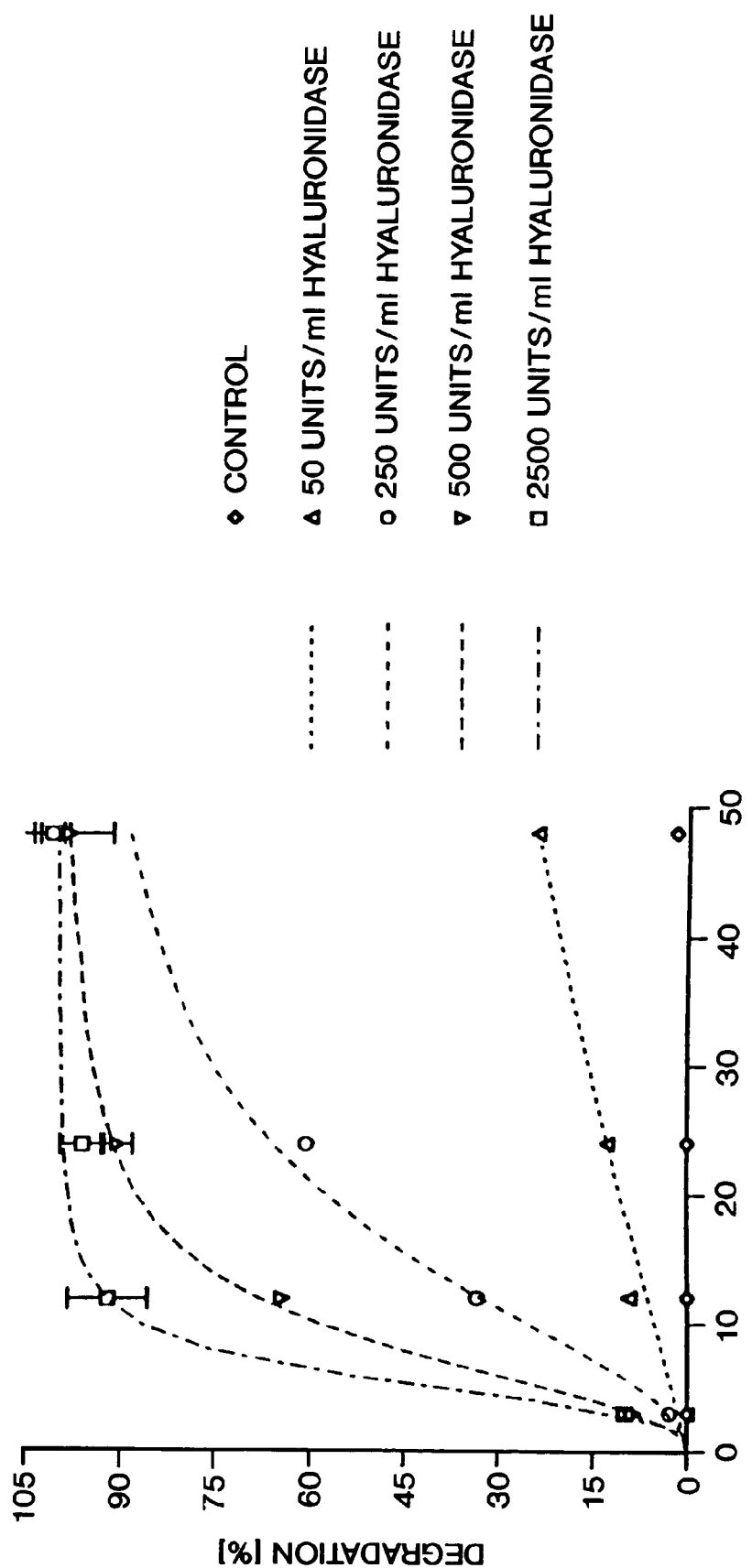
In FIG. 4A, HA-hydrogels were formed by crosslinking 12 mg/ml highly modified (~65–70%) HA-amine (adipic dihydrazido-HA) with 15 mg/ml $(SPA)_2$-PEG. Gels were incubated with different concentrations of bovine testicular hyaluronidase for the indicated time and the degradation of the gels was measured by the release of glucuronic acid into the supernatant using the carbazole method (Bitter and Muir, *Anal Biochem.* 4, 330–334 (1962)).
Figure 4B:
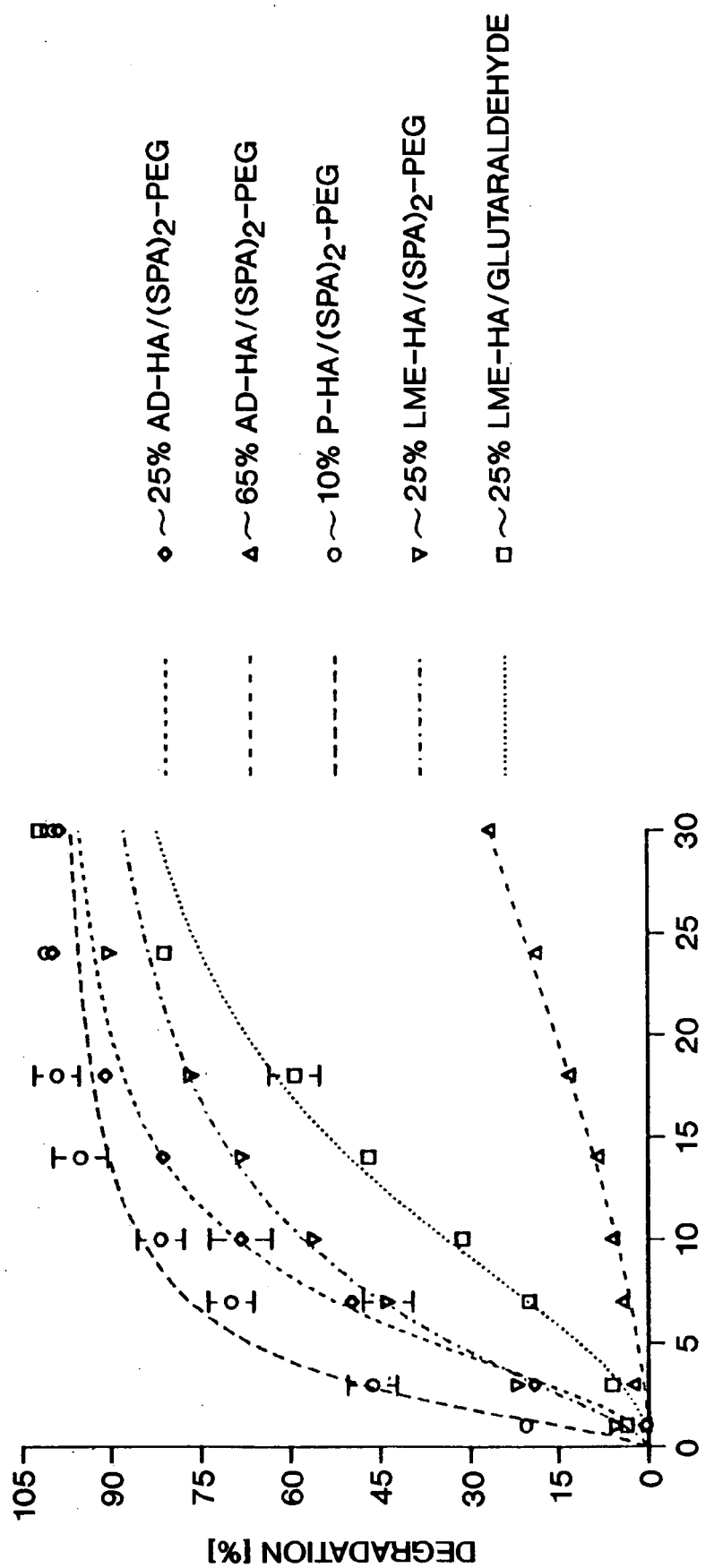
In FIG. 4B, HA-hydrogels were formed by crosslinking 12 mg/ml optimally modified (~20–25%) HA-amine (adipic dihydrazido-HA) with 15 mg/ml $(SPA)_2$-PEG (◊); 12 mg/ml highly modified (~65–70%) adipic dihydrazido-HA with 15 mg/ml $(SPA)_2$-PEG (Δ); 12 mg/ml optimally modified (~20–25%) lysine methylester-HA with either 15 mg/ml $(SPA)_2$-PEG (Λ) or 0.44 mg/ml glutaraldehyde (□), and 12 mg/ml optimally modified (~10–15%) diaminobutyl-HA with 15 mg/ml $(SPA)_2$-PEG (o). Gels were incubated with different concentrations of bovine testicular hyaluronidase for the indicated time and the degradation of the gels was measured as in FIG. 4A above.

Crosslinking of the HA-amine derivatives (Mr~10$^6$) with bifunctional active esters, e.g. polyethyleneglycol-bis-succinimidyl-propionate [(SPA)$_2$-PEG] and reducible 3,3'-dithiobis(sulfo-succinimidyl-propionate) (DTSSP) (Scheme 4), or bifunctional aldehydes, e.g. glutaraldehyde (Scheme 5), generated excellent hydrogels. Stable gels could be formed by crosslinking 5 to 25 mg/ml HA derivative with >0.05 mM aldehyde or >0.2 mM active ester (numbers are reflecting functional group concentrations). Optimal gels were generated by crosslinking 10–15 mg/ml HA derivative, modified to a degree of about 10–25%, with about 0.2 mM aldehyde or 0.6 mM active ester. Similarly, crosslinking of the HA-aldehyde derivatives (Mr~10$^6$) (optimally about 10–15 mg/ml) with bifunctional amines (optimally about 0.2 mM) yielded excellent gels (Scheme 6). Conjugated amines such as dihydrazines or benzylamines are required for in situ polymerization of HA in this case to resonance stabilize the instable Schiff base product formed by reaction of an aldehyde with a primary amine (i.e. hydrazines yield a more stable hydrazone linkage). Hydrogels were also formed from an equimolar mixture of HA-aldehyde derivatives and the different HA-amine derivatives (Scheme 6). Optimal gels were formed with ~15 mg/ml of the HA derivatives. At the optimal concentrations of HA and crosslinker, gelation occurred typically in about 30 sec. to 5 min. which is suitable for in situ polymerization. The crosslinked HA hydrogels were sensitive to glycosidases, i.e. testicular hyaluronidase, indicating that they are biodegradable (FIG. 4).

Figure 5A:
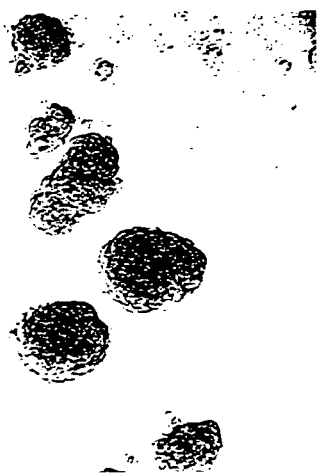
FIG. 5A: Dedifferentiated chondrocytes cultured on a hydrogel formed from highly modified (~65–70%) HA-amine (adipic dihydrazido-HA) crosslinked with 5 mg/ml $(SPA)_2$-PEG aggregate as a consequence of inability to adhere to substratum.
Figure 5B:
FIG. 5B: Cells cultured on a hydrogel made up by the same HA-amine crosslinked with 0.25 mg/ml glutaraldehyde show a rounded morphology and no aggregation indicating that they are able to adhere to the substratum.
Figure 5C:
FIG. 5C: Cells cultured on a hydrogel formed from the HA-amine (adipic dihydrazido-HA) modified to a degree of ~20–25% and crosslinked with 2 mg/ml $(SPA)_2$-PEG adhere to the substratum, spread and subsequently infiltrate the hydrogel. All images show cells 24 h post seeding but morphology remains the same even after several days in culture.

A number of different tests including cell culture assays and animal experiments served to assess biocompatibilty of the formulated biomaterials. Embedding of chondrocytes into the polymerizing HA hydrogels showed that neither aldehyde nor NHS-ester-mediated crosslinking was toxic to cells at the concentrations employed. Seeding of cells on top of prepolymerized HA hydrogels showed a wide variety of cellular behaviours depending on the nature of the crosslinker and crosslinking density (FIG. 5). Highly crosslinked HA hydrogels were impenetrable to cells (FIGS. 5, A and B), while optimally crosslinked gels were infiltrated (FIG. 5C). Supplementation of the HA hydrogels with cell adhesion molecules such as fibronectin (in the range of 0.1 to 1 mg/ml) did induce adhesion and spreading of cells on the materials independent of the nature of the crosslinker and the crosslinking density, but did not change the results with regard to cell infiltration, demonstrating that the lack of infiltration is due to the high crosslinking density and not the absence of cell-matrix interactions. See below and FIG. 7.

Figure 6A:
FIG. 6 shows in vivo evaluation of HA hydrogels formed from different HA derivatives using aldehyde-mediated crosslinking. Subcutaneous implantation in rats of HA hydrogels consisting of (FIG. 6A) 12 mg/ml optimally modified (~20–25%) HA-amine (adipic dihydrazido-HA) crosslinked with 0.25 mg/ml glutaraldehyde, (FIG. 6B) 7 mg/ml of the same HA-amine crosslinked with 7 mg/ml HA-aldehyde (periodate oxidized), (FIG. 6C) 7 mg/ml of the same HA-amine crosslinked with 7 mg/ml HA-aldehyde (deprotected amino-dimethyl acetal-HA, ~10–15% modified), or (FIG. 6D) 7 mg/ml of the same HA-amine crosslinked with 7 mg/ml HA-aldehyde (deprotected hydrazido-dimethyl acetal-HA, ~40–45% modified). The hydrogels also contained 1 mg/ml prefibrillized intact collagen type I, 200 μg/ml BMP-2 and 500 ng/ml IGF-1 to induce bone formation. Tissue specimens were harvested 10 days post implantation, fixed in formalin and processed for histology by paraffin embedding. Sections were stained with Haematoxylin/Eosin. m, matrix material (note: matrix material shrinks during dehydration); s, skin (indicates orientation of implant).
Figure 6B:
Figure 6C:
Figure 6D:
Figure 8B:
FIG. 8 shows differential effect of growth factors incorporated into HA hydrogels on tissue transformation. Subcutaneous implantation in rats of the HA hydrogel formed from 12 mg/ml optimally modified (~20–25%) HA-amine (adipic dihydrazido-HA) crosslinked with 15 mg/ml $(SPA)_2$-PEG. The hydrogels also contained 1 mg/ml prefibrillized intact collagen type I, and were supplemented either with 200 μg/ml BMP-2 and 500 ng/ml IGF-1 (FIG. 8A), or 200 μg/ml BMP-2 and 50 ng/ml TGF-β2 (FIG. 8B). Tissue specimens were harvested 10 days post implantation, fixed in formalin and processed for histology by paraffin embedding. Sections were stained with Haematoxylin/Eosin.
Figure 8D:
Figure 8A:
Figure 8C:

Subcutaneous implantation of biomaterials in rats is the established model for evaluation of biocompatibility of biomaterials (Laurencin et al., *J. Biomed. Mat. Res.* 24, 1463–1481 (1990)) and for induction of ectopic bone formation by members of the TGF-β gene family, and bone morphogenetic proteins (BMP) in particular (Wang et al., *Proc. Natl. Acad. Sci. U.S.A.* 87, 2220–2224 (1990); Sampath et al., *J. Biol. Chem.* 267, 20352–20362 (1992)). Taking into consideration the cell culture results, we have formulated a number of HA hydrogels for in vivo biocompatibility testing in this model. Implantation of prepolymerized HA hydrogel discs loaded with recombinant BMP-2 and IGF-1 or TGF-β2 subcutaneously in rats showed a mild fibrosis with a varying degree of cartilage and bone formation depending on the nature of the HA biomaterial (FIGS. 6 and 7). The growth factors were mixed with the HA derivatives prior to gelling and the induction of bone formation suggests that neither reaction mechanism used for HA crosslinking (aldehyde or active ester-mediated reactions) significantly affected the biological activity of the growth factors. Little inflammation was observed with active ester crosslinked HA-amine derivatives (FIG. 7) or with HA-amine derivatives crosslinked with various HA-aldehyde derivatives (FIGS. 6B–6D) while a stimulation of foreign body giant cells was seen when the same HA-amine derivatives were crosslinked with glutaraldehyde (FIG. 6A). The degree of modification of HA strongly affected the resorption and transformation rate of the biomaterials (FIGS. 7A, 7B). Nevertheless, limited bone formation was seen even with a biomaterial formed from a highly modified (65–70%) HA-amine derivative (FIG. 7A). The absence of bone formation with a smaller bifunctional NHS-ester crosslinker indicates that the size of the generated crossbridge is crucial for resorption and cellular infiltration (FIG. 7C). This is probably due to the difference in pore size of the material formed with crosslinkers of different sizes. The infiltration and transformation rate was similar with BMP-2/IGF-1 and BMP-2/TGF-β2 loaded biomaterials, indicating that the resorption rate is a material property. However, at ten days post-implantation, the newly formed tissue was largely cartilage in the first group and largely bone in the second group (FIG. 8), exemplifying the angiogenic effect of TGF-β2 (Yang and Moses, *J. Cell. Biol.*, 111, 731–741 (1990)). This demonstrates that the biological activity of the HA material can be modulated by inclusion of different bioactive factors. The lack of significant adverse effects and the demonstration of the desired biological activity of these novel HA biomaterials in vivo demonstrates their usefulness as a delivery vehicle for cells and growth factors in the field of tissue regeneration.

There are several approaches to the production of HA, including extraction from tissue and biosynthesis. Extraction from tissue typically uses fresh or frozen cocks' combs (U.S. Pat. No. 5,336,767), although other tissues including the synovial fluid of joints (Kvam et al., *Anal. Biochem.* 211, 44–49 (1993)), human umbilical cord tissue, bovine vitreous humor, and bovine tracheae, have been used. It is also possible to prepare HA by microbiological methods, such as by cultivating a microorganism belonging to the genus Streptococcus which is anhemolytic and capable of producing HA in a culture medium (U.S. Pat. Nos. 4,897,349; 4,801,539; 4,780,414; 4,517,295; 5,316,926). The HA raw material for preparing the compositions of the invention preferably consists of high molecular weight HA, more preferably of molecular weight greater than 0.5 million daltons, and more preferably of molecular weight greater than one million daltons. The HA raw material for the compositions of examples of this invention described herein was obtained from Genzyme Corp. (Cambridge, Mass.), and had a molecular weight greater than one million daltons. The size of the HA was unchanged after derivatization.

The compositions of the invention have many therapeutic uses. The fact that the compositions may be cured in a surgically practical time frame of one to five minutes in situ with concurrent crosslinking to the tissue surfaces allows for employment as a tissue glue. Many situations in various surgical applications require such adhesives. For example, the compositions of the invention may be used to stem hemorrhage in general surgery, reconstruct nerves and vessels in reconstructive, neuro- and plastic surgery, and to anchor skin, vascular, or cartilage transplants or grafts in orthopedic, vascular, and plastic surgery. Those of skill in the art may choose and design particular embodiments of the invention which are particularly suitable for a desired application, by adjusting several factors, including: (1) the degree of functionalization of HA, which affects the crosslinking density of the material and interaction with cellular proteins, including receptors and glycosidases; (2) the concentration of the crosslinker, which affects the crosslinking density of the material; (3) the size of the generated cross-bridge, which affects the pore size of the material; (4) the nature of the crosslinking mechanism, which determines polymerization time and the specificity of the reaction; and (5) the nature of the cross-bridge, which provides biological cues. See FIGS. 4, 5, and 7 for data concerning HA hydrogels with different crosslinking densities and pore sizes. Generally, active ester- or photo-crosslinking are preferred to form materials for applications requiring fast gelation and strong bonding with tissue surfaces, such as tissue glues. Materials with anti-adhesive properties, which are useful to form tissue separations or for tissue augmentation, are formed from highly modified HA derivatives with low molecular weight crossilinkers, which generates a dense material with very small pores, thereby minimizing cell adhesion and infiltration. Conversely, biodegradable scaffolds for tissue repair are formed from HA with a limited degree of derivativization and high molecular weight crosslinkers, which generate a porous, biodegradable material. The crossbridge may even contain biological cues, such as peptide sequences, which facilitate material degradation by, for example, proteolysis or cellular infiltration (e.g., the RGD sequence).

Compositions of this invention were designed to serve as a vehicle for the delivery of cells or bioactive molecules such as growth factors to stimulate focal repair. The crosslinked HA derivatives are porous hydrogels in which biologically or therapeutically active compounds (e.g., growth factors, cytokines, drugs, and the like) can be physically or chemically incorporated. These compounds will then be subject to sustained release by chemical, enzymatic, and physical erosion of the hydrogel and/or the covalent linkage between the HA chain and biologically active compound over a period of time. Local delivery of growth factors with such a scaffold facilitates wound healing and tissue regeneration in many situations. For example, the compositions of the invention may be used not only to promote bone formation and stimulate cartilage repair in orthopedic procedures, as described more fully below, but also to treat pathological wound conditions such as chronic ulcers. They may also serve as a scaffold to generate artificial tissues, e.g., cartilage (Hauselmann et al., *Am. J. Physiol.* 271, C742–752 (1996)), through proliferation of autologous cells in culture. Similar procedures for generation of equivalents of other tissues or organs, including skin, liver, and others, in culture may be developed in the future and may be used in combination with the compositions of the invention.

Highly crosslinked materials have an anti-adhesive property with respect to cells, and such compositions may be used to generate tissue separations and to prevent adhesions following surgery. See FIGS. 5A and 7C, showing highly modified HA-amine, i.e., adipic dihyrazido HA, preferably crosslinked with low molecular weight bifunctional NHS-ester. The viscoelastic properties of HA make it particularly well suited for this purpose, and it is used clinically to achieve temporal pain relief by repeated intraarticular injections in arthropathies as a "joint lubricant", and as a protective agent for eye irritations and in ophthalmic surgery. The technique of tissue separation is used in facial reconstruction in plastic surgery and dentistry. Prevention of the formation of adhesions is particularly relevant in reconstructive surgery of tendons, in surgical procedures in the urogenital system, and in thoracic surgery. Many different HA-based materials are already in clinical use in these areas. (See products manufactured by Anika Therapeutics, Inc. (Woburn, Mass.), Biomatrix, Inc. (Ridgefield, N.J.), Genzyme Corp. (Cambridge, Mass.), and Fidia, S.p.A. (Abano Terme, Italy)). Those of skill in the art may choose and design particular embodiments of the invention which are particularly suitable for a desired application by selecting distinct features as outlined above.

The injectable nature of the compositions of the invention also renders them suitable for tissue augmentation in plastic surgery, where the HA matrix serves primarily as a biocompatible filler material, e.g., for filling dermal creases or lip reconstruction. Again, those of skill in the art may choose and design particular embodiments of the invention which are particularly suitable for a desired application, as outlined above.

The half-life of pharmacological compounds, both synthetic and biological, has been shown to be drastically increased when delivered in a form conjugated to HA (Larsen and Balazs, *Adv. Drug Delivery Rev.* 7, 279–293 (1991); Drobnik, J., *Drug Delivery Rev.* 7, 295–308 (1991)). The functionalized forms of HA provided by this invention allow for easy substitution with pharmacologically active agents, such as anti-inflammatories, analgesics, steroids, cardiovascular agents, anti-tumor agents, immunosuppressants, sedatives, anti-bacterial, anti-fungal, and anti-viral agents, etc., and may be used for sustained drug release over time, either locally in hydrogel form or systemically in free form.

In orthopedic surgery, the functionalized forms of HA of this invention have applications as a tissue glue or bioactive matrix material in the treatment of chondral and osteochondral fractures, osteochondritis dissecans, meniscal tears, as well as ruptured ligaments, tendons, or myotendineous junctions. The HA materials of this invention may serve to facilitate anchorage of chondral or osteochondral transplants or grafts, or other biological or artificial implant materials, or to stimulate new bone or cartilage formation by serving as a scaffold for cells or as a delivery vehicle for growth factors. One general approach to promote articular cartilage repair based on the compositions of the invention comprises using: (1) in situ polymerized HA hydrogel as a matrix to fill the defect which is to be repaired and to provide a scaffold for repair cells, (2) an optional chemotactic agent to attract repair cells to the matrix and defect site, or alternatively, autologous chondrocytes or mesenchymal stem cells, (3) an optional factor to promote cellular proliferation of repair cells in the matrix and defect site; (4) sustained release of a transforming factor by the HA hydrogel over time to promote differentiation of the repair cells into chondrocytes which produce new cartilage; and (5) an optional anti-angiogenic factor to prevent vascularization and endochondral ossification of the newly formrred cartilage. Examples of suitable factors are known to those skilled in the art, and may be found in, e.g., U.S. Pat. No. 5,368,858.

Delivery of growth factors in active form may require supplementation of the HA hydrogels with additional ingredients, such as growth factor binding molecules like heparin and collagen. For example, for cartilage repair, crosslinked hyaluronic acid hydrogels that are rapidly infiltrated by cells such as those formed from an HA-amine derivative crosslinked with a polyvalent high molecular weight NHS-ester crosslinker, e.g., $(SPA)_2$-PEG, are selected which are resorbed and replaced by repair tissue within about 2 to 3 weeks. In some cases, cells and/or growth factors may be mixed in prior to gelling.

The following are illustrative examples, which are not intended to limit the scope of the present invention.

EXAMPLES

Example 1

Preparation of N-(2,2-dimethoxyethyl)-4-(methoxycarbonyl)butanamide (1)—EDC (4.98 g, 0.026 mol) was added to a mixture of aminoacetaldehyde dimethyl acetal (2.18 ml, 20 mmol) and methyl monoester of succinic acid (2.64 g, 20 mmol) in 75 ml of dichloromethane, and the reaction mixture stirred for 24 h at room temperature. The solution was extracted successively with 50 ml each of ice cold solutions of 0.75M sulfuric acid, 1M NaCl, saturated sodium bicarbonate, and 1M NaCl. The organic phase was collected and dried with sodium sulfate. The solvent was evaporated under reduced pressure yielding a syrup, which showed a single spot on charring upon TLC in solvent A ($R_f$ 0.75) and solvent B ($R_f$ 0.24). The apparent yield of 1 was 65%. $^1$H NMR in $CDCl_3$ δ 5.70 (bs, 1H, NH), 4.34 [t, 1H, CH—$(OCH_3)$, 3.67

(s, 3H, COOCH$_3$), 3.43–3.35 (s and t, 8H, CH$_3$OC and CHCH$_2$NH), 2.38–2.26 (m, 4H, CH$_2$CO).

Formation of Acyl-hydrazide (2) from 1—Anhydrous hydrazine (248 µl, 7.9 mmol) was added to a solution of 1 (1.73 g, 7.9 mmol) in 5 ml of anhydrous methanol. The mixture was stirred at room temperature overnight and the solvent subsequently evaporated under reduced pressure yielding a solid residue. The residue was dissolved in H$_2$O (6 ml) and extracted three times with an equal volume of dichloromethane. The aqueous solution was evaporated to dryness under reduced pressure and then further dried overnight in vacuo. The crystaline solid (1.04 g, 82% yield) was homogeneous on TLC in solvent A (R$_f$ 0.10) when visualized by charring. The $^1$H NMR spectrum indicated the loss of the ester methoxy group when compared to 1.

Preparation of Hydrazido-dimethyl acetal-HA (formula XIX)—Sodium hyaluronate (100 mg, 0.25 mmol) and N-(2,2-dimethoxyethyl)-4-(hydrazido)butanamide (2) (1.646 g, 7.5 mmol) was dissolved in H$_2$O (40 ml, 2.5 mg/ml HA). The pH was adjusted to 6.5 and HOBT (169 mg, 1.25 mmol) predissolved in a 1:1 mixture of water and DMSO (1 ml) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H$_2$O at a concentration of approximately 5 mg/ml and the precipitation repeated twice. The purified product was freeze dried and kept at 4° C. under N$_2$. See FIG. 2B for NMR data of the product.

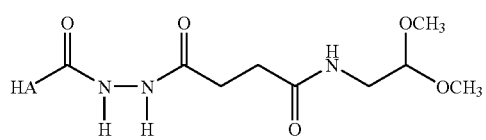

(XIX)

Example 2

Preparation of Aminoacetaldehyde-dimethyl acetal-HA (formula XX)—Sodium hyaluronate (100 mg, 0.25 mmol) and 2,2-dimethoxyethylamine (0.788 g, 7.5 mmol) was dissolved in H$_2$O (40 ml, 2.5 mg/ml HA). The pH was adjusted to 7.5 and NHS.SO$_3$Na (268 mg, 1.25 mmol) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H$_2$O at a concentration of approximately 5 mg/ml and the precipitation repeated twice. The purified product was freeze dried and kept at 4° C. under N$_2$.

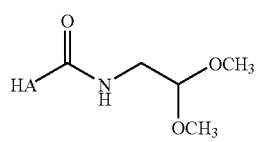

(XX)

Example 3

Deprotection of HA-acetals to form HA-aldehydes—The acetal modified HA(formula XXI) was dissolved in H$_2$O to a concentration of 5–10 mg/ml and 1M HCl was added to give a final concentration of 0.025M. The solution was then allowed to stand at room temperature for 0.5 to 1.0 h. The solution was neutralized by the addition of 1M NaOH, yielding the deprotected HA-aldehyde (formula XXII).

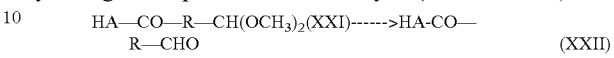

HA—CO—R—CH(OCH$_3$)$_2$(XXI)------>HA-CO—R—CHO    (XXII)

Example 4

Preparation of Diaminoethane-HA (formula XXIII)—Sodium hyaluronate (100 mg, 0.25 mmol) and 1,2-diaminoethane HCl (0.998 g, 7.5 mmol) was dissolved in H$_2$O (40 ml, 2.5 mg/ml HA). The pH was adjusted to 6.5 and HOBT (169 mg, 1.25 mmol) predissolved in a 1:1 mixture of water and DMSO (1 ml) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H$_2$O at a concentration of approximately 5 mg/ml and the precipitation repeated twice. The purified product was freeze dried and kept at 4° C. under N$_2$.

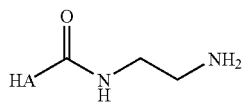

(XXIII)

Example 5

Preparation of L-Lysine methyl ester-HA (formula XXIV)—Sodium hyaluronate (100 mg, 0.25 mmol) and L-lysine methyl ester dihydrochloride (1.748 g, 7.5 mmol) was dissolved in H$_2$O (40 ml, 2.5 mg/ml HA). The pH was adjusted to 6.5 and HOBT (169 mg, 1.25 mmol) predissolved in a 1:1 mixture of water and DMSO (1 ml) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H$_2$O at a concentration of approximately 5 mg/ml and the precipitation repeated twice. The purified product was freeze dried and kept at 4° C. under N$_2$. See FIG. 3C for NMR data of the product.

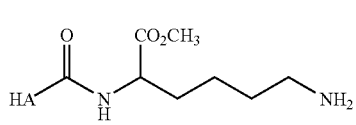

(XXIV)

Example 6

Preparation of L-Histidine methyl ester HA (formula XXV)—Sodium hyaluronate (100 mg, 0.25 mmol) and L-histidine methyl ester dihydrochloride (1.815 g, 7.5 mmol) was dissolved in H₂O (40 ml, 2.5 mg/ml HA). The pH was adjusted to 6.5 and HOBT (169 mg, 1.25 mmol) predissolved in a 1:1 mixture of H₂O and DMSO (1 ml) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H₂O at a concentration of approximately 5 mg/ml and the precipitation repeated twice. The purified product was freeze dried and kept at 4° C. under N₂. See FIG. 3B for NMR data of the product.

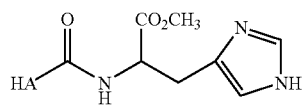

(XXV)

Example 7

Preparation of Hydrazido-HA (formula XXVI)—Sodium hyaluronate (100 mg, 0.25 mmol) and dihydrazide i.e. adipic dihydrazide (1.31 g, 7.5 mmol) was dissolved in H₂O (40 ml, 2.5 mg/ml HA). The pH was adjusted to 6.5 and HOBT (169 mg, 1.25 mmol) predissolved in a 1:1 mixture of water and DMSO (1 ml) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H₂O at a concentration of approximately 5 mg/ml and the precipitation repeated twice. The purified product was freeze dried and kept at 4° C. under N₂. See FIG. 3D for NMR data of the product.

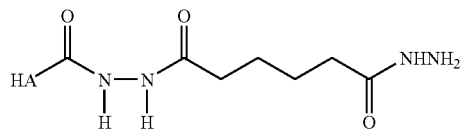

(XXVI)

Example 8

Preparation of Diaminoalkyl-HA (formula XXVII)—Sodium hyaluronate (100 mg, 0.25 mmol) and a diaminoalkane, i.e. 1,2-diaminobutane HCl (1.208 g, 7.5 mmol) was dissolved in H₂O (40 ml, 2.5 mg/ml HA). The pH was adjusted to 7.5 and NHS.SO₃Na (268 mg, 1.25 mmol) and EDC (240 mg, 1.25 mmol) was added and the reaction mixture was stirred overnight. The pH was subsequently adjusted to 7.0 with 1M NaOH and NaCl added to produce a 5% w/v solution. HA was precipitated by addition of three volume equivalents of ethanol. The precipitate was redissolved in H₂O at a concentration of approximately 5 mg/ml and the precipitation repeated twice. The purified product was freeze dried and kept at 4° C. under N₂. See FIG. 3A for NMR data of the product.

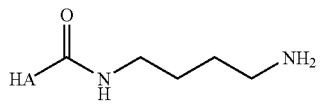

(XXVII)

Example 9

Formation of crosslinked HA hydrogels—The general procedure for forming crosslinked HA hydrogels is as follows: Modified HA is dissolved by agitation in H₂O or phosphate buffered saline (pH 7.4–8.5) at a concentration of 5–25 mg/ml. The degree of modification of the HA derivative is derived from the integration of the ¹H NMR peaks. After complete dissolution, the HA derivative solution is transferred to a 1 ml syringe. When reacting the HA derivatives with low molecular weight crosslinkers, a slight excess of the compound (about 1.1 molar equivalent of functional groups) is dissolved in a second 1 ml syringe in 1/10 of the HA derivative volume immediately prior to use. The syringes are connected while paying special attention to excluded air, the contents are rapidly mixed, typically with 20 passages, and then extruded. When reacting HA derivative molecules with different functionalities, 0.5–1.0 equivalent of HA-aldehyde is mixed with 1 equivalent of HA-hydrazine, depending on the degree of modification of the HA derivatives. At room temperature, gelation occurs within about 30 seconds to several minutes, depending on the formulation, and the gel properties do not significantly change after approximately 5 minutes.

Example 10

Digestion of crosslinked HA hydrogels with hyaluronidase—The general procedure for digestion of crosslinked HA hydrogels is as follows: HA hydrogels are formed in 1 mL syringes by crosslinking 12 mg/ml HA-amine in phosphate buffered saline with various crosslinkers as indicated in FIG. 4. Gelling is allowed to occur for 1 hour at 37° C. for the reaction to be complete, after which identical ~100 µl cylindrical gels are formed by cutting the syringes with a razor blade. The gels are incubated with different concentrations of bovine testicular hyaluronidase (Sigma) 50–5000 U/mL in 400 µl of 30 mM citric acid, 150 mM Na₂HPO₄, pH 6.3, 150 mM NaCl for the indicated time 0–48 hours. Degradation of the gels is determined from the release of glucuronic acid into the supernatant as measured using the carbazole method (Bitter and Muir, supra). See FIG. 4.

Example 11

Crosslinked HA hydrogels as a matrix for cell culture—Chondrocytes were isolated from bovine nose cartilage according to established procedures (Häuselmann et al., Matrix 12, 116–129 (1992); Küttner et al., J. Cell Biol. 93, 743–750 (1982)), cultured Ham's F12 medium containing 5% fetal bovine serum and antibiotics, and dedifferentiated by monolayer culture on plastic. For cytotoxicity studies, cells (2.5×10⁵) were embedded into the HA hydrogels by gently mixing the trypsinized cells (about 50 to 100 µl) with the polymerizing HA and crosslinker mixture (approximately 400 µl gel volume) prior to complete setting. Agarose embedded cells served as a control. After adaptation to the culture conditions (24 h), cell proliferation and metabolic activity was assessed by pulse labeling with [$^3$H]thymidine and [$^{35}$S]methionine. For cell infiltration studies, HA hydrogels were polymerized in 24-well plates (~15 mm diameter and 3 mm height) for 1 h at room temperature, and extensively rinsed with phosphate buffered saline. Cell adhesion molecules or chemotactic factors, e.g. IGF-1, were added to the HA solution prior to crosslinking when desired. After 24 h, cells ($2.5\times10^5$) were seeded on top of the HA-hydrogels and cultured as above. At different time points post seeding, gels were fixed in phosphate buffered 4% paraformaldehyde and processed for paraffin embedding. Cell infiltration was assessed by staining sections with Haematoxylin/Eosin. See FIG. 5.

Example 12

Subcutaneous implantation of HA hydrogels in rats—Rats (2–3 per test material) were anaesthetized with ketamine/xylazine, the ventral thorax and abdomen shaved, and prepared aseptically. A small vertical incision was made on either side of the xiphoid cartilage of the sternum and the skin undermined with a blunt instrument to separate the skin from the underlying tissue. HA hydrogels were polymerized in 3 ml syringes as described. For induction of chondroosseous differentiation, 1 mg/ml prefibrillized intact collagen type I (Organogenesis, Canton, Mass.), 200 µg/ml recombinant BMP-2 (Genetics Institute, Cambridge, Mass.), and 500 ng/ml IGF-1 (Celtrix Pharmaceuticals, Santa Clara, Calif.) or 50 ng/ml TGF-β2 (Celtrix Pharmaceuticals, Santa Clara, Calif.) were mixed with the HA solution prior to crosslinking. Collagen fibrils were prepared by slow polymerization (from dilute solutions of 2–3 mg/ml) of acid-solubilized collagen in phosphate buffered saline and harvested by centrifugation following standard protocols (McPherson et al., *Collagen Rel. Res.* 5, 119–135 (1985)). Gelling of the HA hydrogels was allowed to occur for 24 h at room temperature for the reaction to be complete, after which identical ~3 mm thick cylindrical gels were prepared by cutting the syringes with a razor blade. HA hydrogel discs were then placed in each pocket and the skin incisions closed with sutures. Ten days post operatively, the rats were euthanized and the appearance of the implant sites, i.e. degree of inflammation, grossly examined and tissue specimens harvested and processed for histology by fixation in phosphate buffered formalin and paraffin embedding. Sections were stained with Haematoxylin/Eosin and with Safranin-O/fast green, and cell infiltration and transformation (cartilage and bone formation) induced by the biomaterial as well as signs of fibrosis and inflammation in the surrounding tissue evaluated. See FIGS. 6–8.

We claim:
1. A method for making a derivative of hyaluronic acid (HA), comprising the steps of:
    a) forming an activated ester at a carboxylate of a glucuronic acid moiety of hyaluronic acid;
    b) substituting at the carbonyl carbon of the activated ester formed in step (a), a side chain comprising a nucleophilic portion and a functional group portion; and
    c) forming a cross-linked hydrogel from the functional group portion of the hyaluronic acid derivative in solution under physiological conditions wherein the forming of a cross-linked hydrogel is not by photo-cross-linking.
2. The method of claim 1, wherein the nucleophilic portion is selected from the group consisting of primary amine, and secondary amine.
3. The method of claim 1, wherein the functional group portion is selected from the group consisting of active ester, aldehyde, amine, hydrazide, maleimide, sulfhydryl, and peptide.
4. The method of claim 1, wherein step (a) is performed with an active ester selected from the group consisting of a substituted triazole, N-sulfosuccinimide, nitrophenol, partially halogenated phenol, perhalophenol, pentafluorophenol, HOBT, and NHS, by carbodiimide-mediated coupling.
5. The method of claim 1, wherein step (c) is performed in situ in a patient in need of tissue repair.
6. A method for forming a matrix for a temporary scaffold for tissue repair according to the method of claim 1, wherein a crosslinker is used in step c), and wherein the crosslinker is selected from the group consisting of polyvalent active ester, aldehyde, amine, maleimide, and sulihydryl.
7. A method for forming a matrix for a temporary scaffold for tissue repair according to the method of claim 1, wherein the HA derivative comprises a peptide substrate for transglutaminase, and wherein the HA derivative is crosslinked using transglutaminase.
8. The method of claim 1, wherein step (c) is performed in the presence of cells.
9. The method of claim 1, wherein step (c) is performed in the presence of at least one member selected from the group consisting of growth factors, cytokines, drugs, and bioactive peptides.
10. The method of claim 9, wherein the bioactive peptide RGD is present.
11. The method of claim 9, wherein a bioactive peptide is present and is a substrate for transglutaminase.
12. The method of claim 11, wherein the bioactive peptide APQQEA is present.
13. The method of claim 11, wherein the growth factor TGF-β or BMP is present.

* * * * *